US010253105B2

(12) United States Patent
Takeuchi et al.

(10) Patent No.: US 10,253,105 B2
(45) Date of Patent: Apr. 9, 2019

(54) BISPECIFIC ANTIBODY BINDING TO HUMAN TLR2 AND HUMAN TLR4

(71) Applicant: Astellas Pharma Inc., Chuo-ku, Tokyo (JP)

(72) Inventors: Satoshi Takeuchi, Tokyo (JP); Masahito Sato, Tokyo (JP); Jotarou Suzuki, Tokyo (JP); Shinji Soga, Tokyo (JP); Jun Takasaki, Tokyo (JP); Koji Aoyama, Tokyo (JP); Chie Okuyama, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 63 days.

(21) Appl. No.: 15/121,567

(22) PCT Filed: Feb. 27, 2015

(86) PCT No.: PCT/JP2015/055860
§ 371 (c)(1),
(2) Date: Aug. 25, 2016

(87) PCT Pub. No.: WO2015/129858
PCT Pub. Date: Sep. 3, 2015

(65) Prior Publication Data
US 2016/0355602 A1 Dec. 8, 2016

(30) Foreign Application Priority Data
Feb. 28, 2014 (JP) .................. 2014-038438

(51) Int. Cl.
| C07K 16/28 | (2006.01) |
| C12N 15/63 | (2006.01) |
| C12N 15/64 | (2006.01) |
| C12N 5/12 | (2006.01) |
| C07K 14/705 | (2006.01) |
| A61K 39/395 | (2006.01) |

(52) U.S. Cl.
CPC ............ *C07K 16/2896* (2013.01); *C12N 5/12* (2013.01); *C12N 15/63* (2013.01); *C07K 16/28* (2013.01); *C07K 2317/31* (2013.01); *C07K 2317/40* (2013.01); *C07K 2317/515* (2013.01); *C07K 2317/52* (2013.01); *C07K 2317/56* (2013.01); *C07K 2317/565* (2013.01); *C07K 2317/622* (2013.01); *C07K 2317/64* (2013.01); *C07K 2317/76* (2013.01); *C07K 2317/92* (2013.01); *C07K 2319/00* (2013.01); *C12N 15/64* (2013.01)

(58) Field of Classification Search
CPC .......... A61K 2039/505; A61K 39/3955; A61K 39/39558; C07K 2317/31; C07K 16/2896; C07K 16/468; C07K 2317/76; C07K 16/28; C07K 2317/73; C07K 16/2866; C07K 16/2863; C07K 2317/565
See application file for complete search history.

(56) References Cited

FOREIGN PATENT DOCUMENTS

| WO | WO 01/36488 A1 | 5/2001 |
| WO | WO 2005/019431 A2 | 3/2005 |
| WO | WO 2005/028509 A1 | 3/2005 |
| WO | WO 2005/060368 A2 | 7/2005 |
| WO | WO 2005/065015 A2 | 7/2005 |
| WO | WO 2006/077471 A2 | 7/2006 |
| WO | WO 2007/110678 A2 | 10/2007 |
| WO | WO 2010/107752 A2 | 9/2010 |
| WO | WO 2010/115551 A1 | 10/2010 |
| WO | WO 2011/003925 A1 | 1/2011 |
| WO | WO 2013/072523 A1 | 5/2013 |
| WO | WO 2013/092001 A1 | 6/2013 |
| WO | WO 2013/149111 A2 | 10/2013 |

OTHER PUBLICATIONS

Liu et al. TLR2 and TLR4 in autoimmune diseases: a comprehensive review. Clinic Rev Allerg Immunol 47: 136-147, 2014.*
Supplementary European Search Report dated Sep. 29, 2017, in EP 15754783.7.
International Search Report dated Jun. 2, 2015, in PCT/JP2015/055860.
Shimazu et al., "MD-2, a Molecule that Confers Lipopolysaccharide Responsiveness on Toll-like Receptor 4," J. Exp. Med., Jun. 7, 1999, 189(11):1777-1782.
Spiller et al., "TLR4-induced IFN-γ production increases TLR2 sensitivity and drives Gram-negative sepsis in mice," J. Exp. Med., Aug. 4, 2008, 205(8):1747-1754.

(Continued)

*Primary Examiner* — Bridget E Bunner
(74) *Attorney, Agent, or Firm* — Foley & Lardner LLP

(57) ABSTRACT

The present application provides a bispecific antibody for preventing or treating an immune inflammatory disease by acting on both human TLR2 and human TLR4 to inhibit human TLR2- and human TLR4-mediated immune inflammatory effects. More specifically, the provided bispecific antibody is a bispecific antibody for human TLR2 and human TLR4, including a heavy chain variable region of an anti-human TLR2 antibody consisting of the amino acid sequence of amino acid numbers 1 to 120 of SEQ ID NO: 4; a light chain variable region of an anti-human TLR2 antibody consisting of the amino acid sequence of amino acid numbers 1 to 113 of SEQ ID NO: 6; a heavy chain variable region of an anti-human TLR4 antibody consisting of the amino acid sequence of amino acid numbers 491 to 609 of SEQ ID NO: 4; and a light chain variable region of an anti-human TLR4 antibody consisting of the amino acid sequence of amino acid numbers 625 to 732 of SEQ ID NO: 4.

19 Claims, 2 Drawing Sheets
Specification includes a Sequence Listing.

(56) References Cited

OTHER PUBLICATIONS

Tsukamoto et al,. "Multiple potential regulatory sites of TLR4 activation induced by LPS as revealed by novel inhibitory human TLR4 mAbs," International Immunology, Apr. 12, 2012, 24(8):495-506.
Office Action dated Nov. 4, 2018, in CN 201580011160.9, with English translation.

* cited by examiner

SEQUENCE LISTING

```
<160> NUMBER OF SEQ ID NOS: 10

<210> SEQ ID NO 1
<211> LENGTH: 2199
<212> TYPE: DNA
<213> ORGANISM: Artificial Sequence
<220> FEATURE:
<223> OTHER INFORMATION: anti-human TLR2 heavy chain_anti-human TLR4
      scFv fusion peptide of bispecific antibody
<220> FEATURE:
<221> NAME/KEY: CDS
<222> LOCATION: (1)..(2199)

<400> SEQUENCE: 1 gag gta cag ttg gtg gag agt gga ggc ggg ctg gtc caa cct ggt ggg        48
Glu Val Gln Leu Val Glu Ser Gly Gly Gly Leu Val Gln Pro Gly Gly
1               5                   10                  15 agt ctt cgc ctt tct tgt gca gcc tct ggg ttt acc ttc tca aac tat        96
Ser Leu Arg Leu Ser Cys Ala Ala Ser Gly Phe Thr Phe Ser Asn Tyr
            20                  25                  30 gcc atg tcc tgg gtg cgt cag gct ccc ggc aaa gga ctg gaa tgg gtt       144
Ala Met Ser Trp Val Arg Gln Ala Pro Gly Lys Gly Leu Glu Trp Val
        35                  40                  45 gcc gcc att tat gga cgg ggc ggt tac aca aac tac gca gat tcc gtc       192
Ala Ala Ile Tyr Gly Arg Gly Gly Tyr Thr Asn Tyr Ala Asp Ser Val
    50                  55                  60 aag gga agg ttc aca atc agc cga gac aat tcc aag aac acc ctc tac       240
Lys Gly Arg Phe Thr Ile Ser Arg Asp Asn Ser Lys Asn Thr Leu Tyr
65                  70                  75                  80
```

```
ctg cag atg aat agc ctg aga gcc gag gac act gct gtg tac tac tgc    288
Leu Gln Met Asn Ser Leu Arg Ala Glu Asp Thr Ala Val Tyr Tyr Cys
                85                  90                  95 gct aaa gaa ggc ggt ggc tac agg gac tat ttt gat tat tgg ggc cag    336
Ala Lys Glu Gly Gly Gly Tyr Arg Asp Tyr Phe Asp Tyr Trp Gly Gln
            100                 105                 110 ggg acc ttg gtc acc gtg tcc tca gcc tcc acc aag ggc cca tcg gtc    384
Gly Thr Leu Val Thr Val Ser Ser Ala Ser Thr Lys Gly Pro Ser Val
        115                 120                 125 ttc ccc ctg gca ccc tcc tcc aag agc acc tct ggg ggc aca gcg gcc    432
Phe Pro Leu Ala Pro Ser Ser Lys Ser Thr Ser Gly Gly Thr Ala Ala
    130                 135                 140 ctg ggc tgc ctg gtc aag gac tac ttc ccc gaa ccg gtg acg gtg tcg    480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc    528
Trp Asn Ser Gly Ala Leu Thr Ser Gly Val His Thr Phe Pro Ala Val
                165                 170                 175 cta cag tcc tca gga ctc tac tcc ctt agt agc gtg gtg acc gtg ccc    576
Leu Gln Ser Ser Gly Leu Tyr Ser Leu Ser Ser Val Val Thr Val Pro
            180                 185                 190 tcc agc agc ttg ggc acc cag acc tac atc tgc aac gtg aat cac aag    624
Ser Ser Ser Leu Gly Thr Gln Thr Tyr Ile Cys Asn Val Asn His Lys
        195                 200                 205 ccc agc aac acc aag gtg gac aag aaa gtt gag ccc aaa tct tgt gac    672
Pro Ser Asn Thr Lys Val Asp Lys Lys Val Glu Pro Lys Ser Cys Asp
    210                 215                 220 aaa act cac aca tgc cca ccg tgc cca gca cct gaa ctc ctg ggg gga    720
Lys Thr His Thr Cys Pro Pro Cys Pro Ala Pro Glu Leu Leu Gly Gly
225                 230                 235                 240 ccg tca gtc ttc ctc ttc ccc cca aaa ccc aag gac acc ctc atg atc    768
Pro Ser Val Phe Leu Phe Pro Pro Lys Pro Lys Asp Thr Leu Met Ile
                245                 250                 255 tcc cgg acc cct gag gtc aca tgc gtg gtg gtg gac gtg agc cac gaa    816
Ser Arg Thr Pro Glu Val Thr Cys Val Val Val Asp Val Ser His Glu
            260                 265                 270 gac cct gag gtc aag ttc aac tgg tac gtg gac ggc gtg gag gtg cat    864
Asp Pro Glu Val Lys Phe Asn Trp Tyr Val Asp Gly Val Glu Val His
        275                 280                 285 aat gcc aag aca aag ccg cgg gag gag cag tac aac agc acg tac cgt    912
Asn Ala Lys Thr Lys Pro Arg Glu Glu Gln Tyr Asn Ser Thr Tyr Arg
    290                 295                 300 gtg gtc agc gtc ctc acc gtc ctg cac cag gac tgg ctg aat ggc aag    960
Val Val Ser Val Leu Thr Val Leu His Gln Asp Trp Leu Asn Gly Lys
305                 310                 315                 320 gag tac aag tgc aag gtc tcc aac aaa gcc ctc cca gcc ccc atc gag    1008
Glu Tyr Lys Cys Lys Val Ser Asn Lys Ala Leu Pro Ala Pro Ile Glu
                325                 330                 335 aaa acc atc tcc aaa gcc aaa ggg cag ccc cga gaa cca cag gtg tac    1056
Lys Thr Ile Ser Lys Ala Lys Gly Gln Pro Arg Glu Pro Gln Val Tyr
            340                 345                 350 acc ctg ccc cca tcc cgg gat gag ctg acc aag aac cag gtc agc ctg    1104
Thr Leu Pro Pro Ser Arg Asp Glu Leu Thr Lys Asn Gln Val Ser Leu
        355                 360                 365 acc tgc ctg gtc aaa ggc ttc tat ccc agc gac atc gcc gtg gag tgg    1152
Thr Cys Leu Val Lys Gly Phe Tyr Pro Ser Asp Ile Ala Val Glu Trp
    370                 375                 380 gag agc aat ggg cag ccg gag aac aac tac aag acc acg cct ccc gtg    1200
Glu Ser Asn Gly Gln Pro Glu Asn Asn Tyr Lys Thr Thr Pro Pro Val
385                 390                 395                 400
```

-continued

| | | |
|---|---|---|
| ctg gac tcc gac ggc tcc ttc ttc ctc tac agc aag ctc acc gtg gac<br>Leu Asp Ser Asp Gly Ser Phe Phe Leu Tyr Ser Lys Leu Thr Val Asp<br>                  405                        410                      415 | 1248 |
| aag agc agg tgg cag cag ggg aac gtc ttc tca tgc tcc gtg atg cat<br>Lys Ser Arg Trp Gln Gln Gly Asn Val Phe Ser Cys Ser Val Met His<br>420                            425                            430 | 1296 |
| gag gct ctg cac aac cac tac acg cag aag agc ctc tcc ctg tct ccg<br>Glu Ala Leu His Asn His Tyr Thr Gln Lys Ser Leu Ser Leu Ser Pro<br>             435                        440                      445 | 1344 |
| ggt aaa gga ggt ggc gga tcc ggt ggc ggt gga agt ggc ggt ggt ggg<br>Gly Lys Gly Gly Gly Gly Ser Gly Gly Gly Gly Ser Gly Gly Gly Gly<br>450                            455                            460 | 1392 |
| tcc gga ggc ggt ggc tct ggg ggt ggc gga tct ggc gga ggc ggt tcc<br>Ser Gly Gly Gly Gly Ser Gly Gly Gly Gly Ser Gly Gly Gly Gly Ser<br>465                        470                        475                      480 | 1440 |
| ggt ggg ggc ggc agt gga ggt ggc gga tct gaa gtg cag ctg gtg gag<br>Gly Gly Gly Gly Ser Gly Gly Gly Ser Glu Val Gln Leu Val Glu<br>                        485                        490                      495 | 1488 |
| tct ggg gga ggc ctg gtg cag cct ggc gag tcc ctg aga ctg tcc tgt<br>Ser Gly Gly Gly Leu Val Gln Pro Gly Glu Ser Leu Arg Leu Ser Cys<br>                    500                        505                      510 | 1536 |
| gca gcc tct gga ttc acc ttt gat act tat gcc atg cac tgg gtc cgg<br>Ala Ala Ser Gly Phe Thr Phe Asp Thr Tyr Ala Met His Trp Val Arg<br>             515                        520                      525 | 1584 |
| cag gct cca ggg aag tgc ctg gag tgg gtc gcc ggt att agt tgg aat<br>Gln Ala Pro Gly Lys Cys Leu Glu Trp Val Ala Gly Ile Ser Trp Asn<br>             530                        535                      540 | 1632 |
| agt ggt aac atc ggc tat gcc gac tct gtg aag ggc cga ttc acc atc<br>Ser Gly Asn Ile Gly Tyr Ala Asp Ser Val Lys Gly Arg Phe Thr Ile<br>545                            550                        555                      560 | 1680 |
| tcc aga gac aac tcc aag aac acc ctg tac ctg cag atg aac agt ctg<br>Ser Arg Asp Asn Ser Lys Asn Thr Leu Tyr Leu Gln Met Asn Ser Leu<br>                    565                        570                      575 | 1728 |
| aga gcc gag gac acc gcc gtg tat tac tgt gca aaa gac tgg gat aac<br>Arg Ala Glu Asp Thr Ala Val Tyr Tyr Cys Ala Lys Asp Trp Asp Asn<br>             580                        585                      590 | 1776 |
| tgg aac ctg ttt gac tac tgg ggc cag gga acc ctg gtc acc gtc tcc<br>Trp Asn Leu Phe Asp Tyr Trp Gly Gln Gly Thr Leu Val Thr Val Ser<br>             595                        600                      605 | 1824 |
| tca gga ggc ggt ggt agc ggt ggg ggt ggc tct ggc gga ggt ggc tcc<br>Ser Gly Gly Gly Gly Ser Gly Gly Gly Gly Ser Gly Gly Gly Gly Ser<br>                    610                        615                      620 | 1872 |
| gac atc cag atg acc cag tct cct tcc tcc ctg tct gca tct gtg gga<br>Asp Ile Gln Met Thr Gln Ser Pro Ser Ser Leu Ser Ala Ser Val Gly<br>625                            630                        635                      640 | 1920 |
| gac aga gtc acc atc act tgc cgg gcc agt cag agt att agt agc tgg<br>Asp Arg Val Thr Ile Thr Cys Arg Ala Ser Gln Ser Ile Ser Ser Trp<br>                        645                        650                      655 | 1968 |
| ctg gcc tgg tat cag cag aaa cca ggg aaa gcc cct aag ctc ctg atc<br>Leu Ala Trp Tyr Gln Gln Lys Pro Gly Lys Ala Pro Lys Leu Leu Ile<br>                    660                        665                      670 | 2016 |
| tat aag gcc tct agt ctg gaa agt ggg gtc cca tcc agg ttc agc ggc<br>Tyr Lys Ala Ser Ser Leu Glu Ser Gly Val Pro Ser Arg Phe Ser Gly<br>             675                        680                      685 | 2064 |
| agt gga tct ggg aca gac ttc act ctg acc atc agc agc ctg cag cct<br>Ser Gly Ser Gly Thr Asp Phe Thr Leu Thr Ile Ser Ser Leu Gln Pro<br>690                            695                        700 | 2112 |
| gag gat ttt gca act tat tac tgc cag cag tat agt agt tat tcc tgg<br>Glu Asp Phe Ala Thr Tyr Tyr Cys Gln Gln Tyr Ser Ser Tyr Ser Trp | 2160 |

```
                        705                 710                 715                 720
                        acc ttc ggc tgc ggg acc aag gtg gaa atc aaa cgt tga                        2199
                        Thr Phe Gly Cys Gly Thr Lys Val Glu Ile Lys Arg
                                            725                 730

<210> SEQ ID NO 2
<211> LENGTH: 732
<212> TYPE: PRT
<213> ORGANISM: Artificial Sequence
<220> FEATURE:
<223> OTHER INFORMATION: anti-human TLR2 heavy chain_anti-human TLR4
      scFv fusion peptide of bispecific antibody

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Ala Ile Tyr Gly Arg Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Gly Gly Tyr Arg Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Gly Ser Gly Gly Gly Gly
            450                 455                 460

Ser Gly Gly Gly Gly Ser Gly Gly Gly Gly Ser Gly Gly Gly Gly Ser
465                 470                 475                 480

Gly Gly Gly Gly Ser Gly Gly Gly Ser Glu Val Gln Leu Val Glu
                    485                 490                 495

Ser Gly Gly Gly Leu Val Gln Pro Gly Glu Ser Leu Arg Leu Ser Cys
            500                 505                 510

Ala Ala Ser Gly Phe Thr Phe Asp Thr Tyr Ala Met His Trp Val Arg
            515                 520                 525

Gln Ala Pro Gly Lys Cys Leu Glu Trp Val Ala Gly Ile Ser Trp Asn
            530                 535                 540

Ser Gly Asn Ile Gly Tyr Ala Asp Ser Val Lys Gly Arg Phe Thr Ile
545                 550                 555                 560

Ser Arg Asp Asn Ser Lys Asn Thr Leu Tyr Leu Gln Met Asn Ser Leu
            565                 570                 575

Arg Ala Glu Asp Thr Ala Val Tyr Tyr Cys Ala Lys Asp Trp Asp Asn
            580                 585                 590

Trp Asn Leu Phe Asp Tyr Trp Gly Gln Gly Thr Leu Val Thr Val Ser
            595                 600                 605

Ser Gly Gly Gly Gly Ser Gly Gly Gly Gly Ser Gly Gly Gly Gly Ser
610                 615                 620

Asp Ile Gln Met Thr Gln Ser Pro Ser Ser Leu Ser Ala Ser Val Gly
625                 630                 635                 640

Asp Arg Val Thr Ile Thr Cys Arg Ala Ser Gln Ser Ile Ser Ser Trp
            645                 650                 655

Leu Ala Trp Tyr Gln Gln Lys Pro Gly Lys Ala Pro Lys Leu Leu Ile
            660                 665                 670

Tyr Lys Ala Ser Ser Leu Glu Ser Gly Val Pro Ser Arg Phe Ser Gly
            675                 680                 685

Ser Gly Ser Gly Thr Asp Phe Thr Leu Thr Ile Ser Ser Leu Gln Pro
            690                 695                 700

Glu Asp Phe Ala Thr Tyr Tyr Cys Gln Gln Tyr Ser Ser Tyr Ser Trp
705                 710                 715                 720

Thr Phe Gly Cys Gly Thr Lys Val Glu Ile Lys Arg
            725                 730

<210> SEQ ID NO 3
<211> LENGTH: 2199
```

```
<212> TYPE: DNA
<213> ORGANISM: Artificial Sequence
<220> FEATURE:
<223> OTHER INFORMATION: anti-human TLR2 heavy chain_anti-human TLR4
      scFv fusion peptide of bispecific antibody
<220> FEATURE:
<221> NAME/KEY: CDS
<222> LOCATION: (1)..(2199)

<400> SEQUENCE: 3
```

| | | | | | | | | | | | | | | | | |
|---|---|---|---|---|---|---|---|---|---|---|---|---|---|---|---|---|
| gag | gta | cag | ttg | gtg | gag | agt | gga | ggc | ggg | ctg | gtc | caa | cct | ggt | ggg | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |
| agt | ctt | cgc | ctt | tct | tgt | gca | gcc | tct | ggg | ttt | acc | ttc | tca | aac | tat | 96 |
| Ser | Leu | Arg | Leu | Ser | Cys | Ala | Ala | Ser | Gly | Phe | Thr | Phe | Ser | Asn | Tyr | |
| | | 20 | | | | | 25 | | | | | 30 | | | | |
| gcc | atg | tcc | tgg | gtg | cgt | cag | gct | ccc | ggc | aaa | gga | ctg | gaa | tgg | gtt | 144 |
| Ala | Met | Ser | Trp | Val | Arg | Gln | Ala | Pro | Gly | Lys | Gly | Leu | Glu | Trp | Val | |
| | 35 | | | | | 40 | | | | | 45 | | | | | |
| gcc | gcc | att | tat | gga | cgg | ggc | ggt | tac | aca | aac | tac | gca | gat | tcc | gtc | 192 |
| Ala | Ala | Ile | Tyr | Gly | Arg | Gly | Gly | Tyr | Thr | Asn | Tyr | Ala | Asp | Ser | Val | |
| 50 | | | | | 55 | | | | | 60 | | | | | | |
| aag | gga | agg | ttc | aca | atc | agc | cga | gac | aat | tcc | aag | aac | acc | ctc | tac | 240 |
| Lys | Gly | Arg | Phe | Thr | Ile | Ser | Arg | Asp | Asn | Ser | Lys | Asn | Thr | Leu | Tyr | |
| 65 | | | | 70 | | | | | 75 | | | | | 80 | | |
| ctg | cag | atg | aat | agc | ctg | aga | gcc | gag | gac | act | gct | gtg | tac | tac | tgc | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |
| gct | aaa | gaa | ggc | ggt | ggc | tac | agg | gac | tat | ttt | gat | tat | tgg | ggc | cag | 336 |
| Ala | Lys | Glu | Gly | Gly | Gly | Tyr | Arg | Asp | Tyr | Phe | Asp | Tyr | Trp | Gly | Gln | |
| | | | 100 | | | | | 105 | | | | | 110 | | | |
| ggg | acc | ttg | gtc | acc | gtg | tcc | tca | gcc | tcc | acc | aag | ggc | cca | tcg | gtc | 384 |
| Gly | Thr | Leu | Val | Thr | Val | Ser | Ser | Ala | Ser | Thr | Lys | Gly | Pro | Ser | Val | |
| | | 115 | | | | | 120 | | | | | 125 | | | | |
| ttc | ccc | ctg | gca | ccc | tcc | tcc | aag | agc | acc | tct | ggg | ggc | aca | gcg | gcc | 432 |
| Phe | Pro | Leu | Ala | Pro | Ser | Ser | Lys | Ser | Thr | Ser | Gly | Gly | Thr | Ala | Ala | |
| | 130 | | | | | 135 | | | | | 140 | | | | | |
| ctg | ggc | tgc | ctg | gtc | aag | gac | tac | ttc | ccc | gaa | ccg | gtg | acg | gtg | tcg | 480 |
| Leu | Gly | Cys | Leu | Val | Lys | Asp | Tyr | Phe | Pro | Glu | Pro | Val | Thr | Val | Ser | |
| 145 | | | | 150 | | | | | 155 | | | | | 160 | | |
| tgg | aac | tca | ggc | gcc | ctg | acc | agc | ggc | gtg | cac | acc | ttc | ccg | gct | gtc | 528 |
| Trp | Asn | Ser | Gly | Ala | Leu | Thr | Ser | Gly | Val | His | Thr | Phe | Pro | Ala | Val | |
| | | | 165 | | | | | 170 | | | | | 175 | | | |
| cta | cag | tcc | tca | gga | ctc | tac | tcc | ctt | agt | agc | gtg | gtg | acc | gtg | ccc | 576 |
| Leu | Gln | Ser | Ser | Gly | Leu | Tyr | Ser | Leu | Ser | Ser | Val | Val | Thr | Val | Pro | |
| | | 180 | | | | | 185 | | | | | 190 | | | | |
| tcc | agc | agc | ttg | ggc | acc | cag | acc | tac | atc | tgc | aac | gtg | aat | cac | aag | 624 |
| Ser | Ser | Ser | Leu | Gly | Thr | Gln | Thr | Tyr | Ile | Cys | Asn | Val | Asn | His | Lys | |
| | 195 | | | | | 200 | | | | | 205 | | | | | |
| ccc | agc | aac | acc | aag | gtg | gac | aag | aaa | gtt | gag | ccc | aaa | tct | tgt | gac | 672 |
| Pro | Ser | Asn | Thr | Lys | Val | Asp | Lys | Lys | Val | Glu | Pro | Lys | Ser | Cys | Asp | |
| 210 | | | | 215 | | | | | 220 | | | | | | | |
| aaa | act | cac | aca | tgc | cca | ccg | tgc | cca | gca | cct | gaa | gcc | gct | ggg | gga | 720 |
| Lys | Thr | His | Thr | Cys | Pro | Pro | Cys | Pro | Ala | Pro | Glu | Ala | Ala | Gly | Gly | |
| 225 | | | | 230 | | | | | 235 | | | | | 240 | | |
| ccg | tca | gtc | ttc | ctc | ttc | ccc | cca | aaa | ccc | aag | gac | acc | ctc | atg | gcc | 768 |
| Pro | Ser | Val | Phe | Leu | Phe | Pro | Pro | Lys | Pro | Lys | Asp | Thr | Leu | Met | Ala | |
| | | | 245 | | | | | 250 | | | | | 255 | | | |
| tcc | cgg | acc | cct | gag | gtc | aca | tgc | gtg | gtg | gtg | gac | gtg | agc | cac | gaa | 816 |
| Ser | Arg | Thr | Pro | Glu | Val | Thr | Cys | Val | Val | Val | Asp | Val | Ser | His | Glu | |
| | | 260 | | | | | 265 | | | | | 270 | | | | |

-continued

| | | |
|---|---|---|
| gac cct gag gtc aag ttc aac tgg tac gtg gac ggc gtg gag gtg cat<br>Asp Pro Glu Val Lys Phe Asn Trp Tyr Val Asp Gly Val Glu Val His<br>     275                     280                     285 | 864 |
| aat gcc aag aca aag ccg cgg gag gag cag tac aac agc acg tac cgt<br>Asn Ala Lys Thr Lys Pro Arg Glu Glu Gln Tyr Asn Ser Thr Tyr Arg<br>290                     295                     300 | 912 |
| gtg gtc agc gtc ctc acc gtc ctg cac cag gac tgg ctg aat ggc aag<br>Val Val Ser Val Leu Thr Val Leu His Gln Asp Trp Leu Asn Gly Lys<br>305                     310                     315                     320 | 960 |
| gag tac aag tgc aag gtc tcc aac aaa gcc ctc cca gcc ccc atc gag<br>Glu Tyr Lys Cys Lys Val Ser Asn Lys Ala Leu Pro Ala Pro Ile Glu<br>                     325                     330                     335 | 1008 |
| aaa acc atc tcc aaa gcc aaa ggg cag ccc cga gaa cca cag gtg tac<br>Lys Thr Ile Ser Lys Ala Lys Gly Gln Pro Arg Glu Pro Gln Val Tyr<br>340                     345                     350 | 1056 |
| acc ctg ccc cca tcc cgg gat gag ctg acc aag aac cag gtc agc ctg<br>Thr Leu Pro Pro Ser Arg Asp Glu Leu Thr Lys Asn Gln Val Ser Leu<br>                     355                     360                     365 | 1104 |
| acc tgc ctg gtc aaa ggc ttc tat ccc agc gac atc gcc gtg gag tgg<br>Thr Cys Leu Val Lys Gly Phe Tyr Pro Ser Asp Ile Ala Val Glu Trp<br>370                     375                     380 | 1152 |
| gag agc aat ggg cag ccg gag aac aac tac aag acc acg cct ccc gtg<br>Glu Ser Asn Gly Gln Pro Glu Asn Asn Tyr Lys Thr Thr Pro Pro Val<br>385                     390                     395                     400 | 1200 |
| ctg gac tcc gac ggc tcc ttc ttc ctc tac agc aag ctc acc gtg gac<br>Leu Asp Ser Asp Gly Ser Phe Phe Leu Tyr Ser Lys Leu Thr Val Asp<br>                     405                     410                     415 | 1248 |
| aag agc agg tgg cag cag ggg aac gtc ttc tca tgc tcc gtg atg cat<br>Lys Ser Arg Trp Gln Gln Gly Asn Val Phe Ser Cys Ser Val Met His<br>420                     425                     430 | 1296 |
| gag gct ctg cac aac cac tac acg cag aag agc ctc tcc ctg tct ccg<br>Glu Ala Leu His Asn His Tyr Thr Gln Lys Ser Leu Ser Leu Ser Pro<br>                     435                     440                     445 | 1344 |
| ggt aaa gga ggt ggc gga tcc ggt ggc ggt gga agt ggc ggt ggt ggg<br>Gly Lys Gly Gly Gly Gly Ser Gly Gly Gly Gly Ser Gly Gly Gly Gly<br>450                     455                     460 | 1392 |
| tcc gga ggc ggt ggc tct ggg ggt ggc gga tct ggc gga ggc ggt tcc<br>Ser Gly Gly Gly Gly Ser Gly Gly Gly Gly Ser Gly Gly Gly Gly Ser<br>465                     470                     475                     480 | 1440 |
| ggt ggg ggc ggc agt gga ggt ggc gga tct gaa gtg cag ctg gtg gag<br>Gly Gly Gly Gly Ser Gly Gly Gly Gly Ser Glu Val Gln Leu Val Glu<br>                     485                     490                     495 | 1488 |
| tct ggg gga ggc ctg gtg cag cct ggc gag tcc ctg aga ctg tcc tgt<br>Ser Gly Gly Gly Leu Val Gln Pro Gly Glu Ser Leu Arg Leu Ser Cys<br>500                     505                     510 | 1536 |
| gca gcc tct gga ttc acc ttt gat act tat gcc atg cac tgg gtc cgg<br>Ala Ala Ser Gly Phe Thr Phe Asp Thr Tyr Ala Met His Trp Val Arg<br>                     515                     520                     525 | 1584 |
| cag gct cca ggg aag tgc ctg gag tgg gtc gcc ggt att agt tgg aat<br>Gln Ala Pro Gly Lys Cys Leu Glu Trp Val Ala Gly Ile Ser Trp Asn<br>530                     535                     540 | 1632 |
| agt ggt aac atc ggc tat gcc gac tct gtg aag ggc cga ttc acc atc<br>Ser Gly Asn Ile Gly Tyr Ala Asp Ser Val Lys Gly Arg Phe Thr Ile<br>545                     550                     555                     560 | 1680 |
| tcc aga gac aac tcc aag aac acc ctg tac ctg cag atg aac agt ctg<br>Ser Arg Asp Asn Ser Lys Asn Thr Leu Tyr Leu Gln Met Asn Ser Leu<br>                     565                     570                     575 | 1728 |
| aga gcc gag gac acc gcc gtg tat tac tgt gca aaa gac tgg gat aac<br>Arg Ala Glu Asp Thr Ala Val Tyr Tyr Cys Ala Lys Asp Trp Asp Asn<br>580                     585                     590 | 1776 |

-continued

| | | |
|---|---|---|
| tgg aac ctg ttt gac tac tgg ggc cag gga acc ctg gtc acc gtc tcc<br>Trp Asn Leu Phe Asp Tyr Trp Gly Gln Gly Thr Leu Val Thr Val Ser<br>      595                             600                    605 | 1824 |
| tca gga ggc ggt ggt agc ggt ggg ggt ggc tct ggc gga ggt ggc tcc<br>Ser Gly Gly Gly Gly Ser Gly Gly Gly Gly Ser Gly Gly Gly Gly Ser<br>   610                         615                    620 | 1872 |
| gac atc cag atg acc cag tct cct tcc tcc ctg tct gca tct gtg gga<br>Asp Ile Gln Met Thr Gln Ser Pro Ser Ser Leu Ser Ala Ser Val Gly<br>625                          630                    635                    640 | 1920 |
| gac aga gtc acc atc act tgc cgg gcc agt cag agt att agt agc tgg<br>Asp Arg Val Thr Ile Thr Cys Arg Ala Ser Gln Ser Ile Ser Ser Trp<br>                 645                    650                    655 | 1968 |
| ctg gcc tgg tat cag cag aaa cca ggg aaa gcc cct aag ctg ctg atc<br>Leu Ala Trp Tyr Gln Gln Lys Pro Gly Lys Ala Pro Lys Leu Leu Ile<br>             660                    665                    670 | 2016 |
| tat aag gcc tct agt ctg gaa agt ggg gtc cca tcc agg ttc agc ggc<br>Tyr Lys Ala Ser Ser Leu Glu Ser Gly Val Pro Ser Arg Phe Ser Gly<br>           675                    680                    685 | 2064 |
| agt gga tct ggg aca gac ttc act ctg acc atc agc agc ctg cag cct<br>Ser Gly Ser Gly Thr Asp Phe Thr Leu Thr Ile Ser Ser Leu Gln Pro<br>   690                         695                    700 | 2112 |
| gag gat ttt gca act tat tac tgc cag cag tat agt agt tat tcc tgg<br>Glu Asp Phe Ala Thr Tyr Tyr Cys Gln Gln Tyr Ser Ser Tyr Ser Trp<br>705                          710                    715                    720 | 2160 |
| acc ttc ggc tgc ggg acc aag gtg gaa atc aaa cgt tga<br>Thr Phe Gly Cys Gly Thr Lys Val Glu Ile Lys Arg<br>           725                    730 | 2199 |

<210> SEQ ID NO 4
<211> LENGTH: 732
<212> TYPE: PRT
<213> ORGANISM: Artificial Sequence
<220> FEATURE:
<223> OTHER INFORMATION: anti-human TLR2 heavy chain_anti-human TLR4
    scFv fusion peptide of bispecific antibody

<400> SEQUENCE: 4

Glu Val Gln Leu Val Glu Ser Gly Gly Gly Leu Val Gln Pro Gly Gly
1                  5                        10                    15

Ser Leu Arg Leu Ser Cys Ala Ala Ser Gly Phe Thr Phe Ser Asn Tyr
              20                    25                    30

Ala Met Ser Trp Val Arg Gln Ala Pro Gly Lys Gly Leu Glu Trp Val
        35                    40                    45

Ala Ala Ile Tyr Gly Arg Gly Gly Tyr Thr Asn Tyr Ala Asp Ser Val
  50                    55                    60

Lys Gly Arg Phe Thr Ile Ser Arg Asp Asn Ser Lys Asn Thr Leu Tyr
65                  70                    75                    80

Leu Gln Met Asn Ser Leu Arg Ala Glu Asp Thr Ala Val Tyr Tyr Cys
              85                    90                    95

Ala Lys Glu Gly Gly Gly Tyr Arg Asp Tyr Phe Asp Tyr Trp Gly Gln
        100                   105                 110

Gly Thr Leu Val Thr Val Ser Ser Ala Ser Thr Lys Gly Pro Ser Val
           115                 120                 125

Phe Pro Leu Ala Pro Ser Ser Lys Ser Thr Ser Gly Gly Thr Ala Ala
  130                   135                 140

Leu Gly Cys Leu Val Lys Asp Tyr Phe Pro Glu Pro Val Thr Val Ser
145                150                  155                  160

Trp Asn Ser Gly Ala Leu Thr Ser Gly Val His Thr Phe Pro Ala Val

```
                      165                 170                 175
Leu Gln Ser Ser Gly Leu Tyr Ser Leu Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ala
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Gly Gly Gly Gly Ser Gly Gly Gly Ser Gly Gly Gly Gly
    450                 455                 460
Ser Gly Gly Gly Ser Gly Gly Gly Ser Gly Gly Gly Gly Ser
465                 470                 475                 480
Gly Gly Gly Gly Ser Gly Gly Gly Ser Glu Val Gln Leu Val Glu
                485                 490                 495
Ser Gly Gly Gly Leu Val Gln Pro Gly Glu Ser Leu Arg Leu Ser Cys
            500                 505                 510
Ala Ala Ser Gly Phe Thr Phe Asp Thr Tyr Ala Met His Trp Val Arg
        515                 520                 525
Gln Ala Pro Gly Lys Cys Leu Glu Trp Val Ala Gly Ile Ser Trp Asn
    530                 535                 540
Ser Gly Asn Ile Gly Tyr Ala Asp Ser Val Lys Gly Arg Phe Thr Ile
545                 550                 555                 560
Ser Arg Asp Asn Ser Lys Asn Thr Leu Tyr Leu Gln Met Asn Ser Leu
                565                 570                 575
Arg Ala Glu Asp Thr Ala Val Tyr Tyr Cys Ala Lys Asp Trp Asp Asn
            580                 585                 590
```

```
Trp Asn Leu Phe Asp Tyr Trp Gly Gln Gly Thr Leu Val Thr Val Ser
        595                 600                 605

Ser Gly Gly Gly Ser Gly Gly Gly Ser Gly Gly Gly Ser
    610                 615                 620

Asp Ile Gln Met Thr Gln Ser Pro Ser Ser Leu Ser Ala Ser Val Gly
625                 630                 635                 640

Asp Arg Val Thr Ile Thr Cys Arg Ala Ser Gln Ser Ile Ser Ser Trp
                645                 650                 655

Leu Ala Trp Tyr Gln Gln Lys Pro Gly Lys Ala Pro Lys Leu Leu Ile
            660                 665                 670

Tyr Lys Ala Ser Ser Leu Glu Ser Gly Val Pro Ser Arg Phe Ser Gly
        675                 680                 685

Ser Gly Ser Gly Thr Asp Phe Thr Leu Thr Ile Ser Ser Leu Gln Pro
    690                 695                 700

Glu Asp Phe Ala Thr Tyr Tyr Cys Gln Gln Tyr Ser Ser Tyr Ser Trp
705                 710                 715                 720

Thr Phe Gly Cys Gly Thr Lys Val Glu Ile Lys Arg
                725                 730
```

```
<210> SEQ ID NO 5
<211> LENGTH: 660
<212> TYPE: DNA
<213> ORGANISM: Artificial Sequence
<220> FEATURE:
<223> OTHER INFORMATION: anti-human TLR2 antibody light chain of
      bispecific antibody, and light chain of anti-human TLR2 antibody
<220> FEATURE:
<221> NAME/KEY: CDS
<222> LOCATION: (1)..(660)

<400> SEQUENCE: 5 gat gtc cag atg acc cag agt cct tca tca ctg tcc gca agc gtg gga        48
Asp Val Gln Met Thr Gln Ser Pro Ser Ser Leu Ser Ala Ser Val Gly
1               5                   10                  15 gac agg gtc acc atc aca tgc cgg tcc agc cag tcc ctg gtg ttc agc        96
Asp Arg Val Thr Ile Thr Cys Arg Ser Ser Gln Ser Leu Val Phe Ser
                20                  25                  30 gat gga aac acc tac ctg aat tgg ttt cag cag aag ccc ggg aaa gcc       144
Asp Gly Asn Thr Tyr Leu Asn Trp Phe Gln Gln Lys Pro Gly Lys Ala
            35                  40                  45 cct aag agg ctg atc tat aaa gtg tct aac aga gac agt ggt gtc ccc       192
Pro Lys Arg Leu Ile Tyr Lys Val Ser Asn Arg Asp Ser Gly Val Pro
        50                  55                  60 tct agg ttc tct ggc agt gga tca ggg acc gac ttt act ctg acc att       240
Ser Arg Phe Ser Gly Ser Gly Ser Gly Thr Asp Phe Thr Leu Thr Ile
65                  70                  75                  80 tct agt ctg cag cca gag gat ttc gcc aca tac tat tgt atg cag ggc       288
Ser Ser Leu Gln Pro Glu Asp Phe Ala Thr Tyr Tyr Cys Met Gln Gly
                85                  90                  95 gct cac tgg ccc ctg aca ttt ggt cag ggc act aaa gtc gaa att aag       336
Ala His Trp Pro Leu Thr Phe Gly Gln Gly Thr Lys Val Glu Ile Lys
            100                 105                 110 cgt acg gtg gct gca cca tct gtc ttc atc ttc ccg cca tct gat gag       384
Arg Thr Val Ala Ala Pro Ser Val Phe Ile Phe Pro Pro Ser Asp Glu
        115                 120                 125 cag ttg aaa tct gga act gcc tct gtt gtg tgc ctg ctg aat aac ttc       432
Gln Leu Lys Ser Gly Thr Ala Ser Val Val Cys Leu Leu Asn Asn Phe
    130                 135                 140 tat ccc aga gag gcc aaa gta cag tgg aag gtg gat aac gcc ctc caa       480
Tyr Pro Arg Glu Ala Lys Val Gln Trp Lys Val Asp Asn Ala Leu Gln
```

```
Tyr Pro Arg Glu Ala Lys Val Gln Trp Lys Val Asp Asn Ala Leu Gln
145                 150                 155                 160 tcg ggt aac tcc cag gag agt gtc aca gag cag gac agc aag gac agc       528
Ser Gly Asn Ser Gln Glu Ser Val Thr Glu Gln Asp Ser Lys Asp Ser
            165                 170                 175 acc tac agc ctg agc agc acc ctg acg ctg agc aaa gca gac tac gag       576
Thr Tyr Ser Leu Ser Ser Thr Leu Thr Leu Ser Lys Ala Asp Tyr Glu
        180                 185                 190 aaa cac aaa gtc tac gcc tgc gaa gtc acc cat cag ggc ctg agc tcg       624
Lys His Lys Val Tyr Ala Cys Glu Val Thr His Gln Gly Leu Ser Ser
    195                 200                 205 ccc gtc aca aag agc ttc aac agg gga gag tgt tag                       660
Pro Val Thr Lys Ser Phe Asn Arg Gly Glu Cys
        210                 215

<210> SEQ ID NO 6
<211> LENGTH: 219
<212> TYPE: PRT
<213> ORGANISM: Artificial Sequence
<220> FEATURE:
<223> OTHER INFORMATION: anti-human TLR2 antibody light chain of
      bispecific antibody, and light chain of anti-human TLR2 antibody

<400> SEQUENCE: 6

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val Phe Ser
            20                  25                  30

Asp Gly Asn Thr Tyr Leu Asn Trp Phe Gln Gln Lys Pro Gly Lys Ala
        35                  40                  45

Pro Lys Arg Leu Ile Tyr Lys Val Ser Asn Arg Asp Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Met Gln Gly
                85                  90                  95

Ala His Trp Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 7
<211> LENGTH: 1353
<212> TYPE: DNA
<213> ORGANISM: Artificial Sequence
<220> FEATURE:
<223> OTHER INFORMATION: Heavy chain of anti-human TLR2 antibody
```

```
<220> FEATURE:
<221> NAME/KEY: CDS
<222> LOCATION: (1)..(1353)

<400> SEQUENCE: 7 gag gta cag ttg gtg gag agt gga ggc ggg ctg gtc caa cct ggt ggg      48
Glu Val Gln Leu Val Glu Ser Gly Gly Gly Leu Val Gln Pro Gly Gly
1               5                   10                  15 agt ctt cgc ctt tct tgt gca gcc tct ggg ttt acc ttc tca aac tat      96
Ser Leu Arg Leu Ser Cys Ala Ala Ser Gly Phe Thr Phe Ser Asn Tyr
            20                  25                  30 gcc atg tcc tgg gtg cgt cag gct ccc ggc aaa gga ctg gaa tgg gtt     144
Ala Met Ser Trp Val Arg Gln Ala Pro Gly Lys Gly Leu Glu Trp Val
        35                  40                  45 gcc gcc att tat gga cgg ggc ggt tac aca aac tac gca gat tcc gtc     192
Ala Ala Ile Tyr Gly Arg Gly Gly Tyr Thr Asn Tyr Ala Asp Ser Val
    50                  55                  60 aag gga agg ttc aca atc agc cga gac aat tcc aag aac acc ctc tac     240
Lys Gly Arg Phe Thr Ile Ser Arg Asp Asn Ser Lys Asn Thr Leu Tyr
65                  70                  75                  80 ctg cag atg aat agc ctg aga gcc gag gac act gct gtg tac tac tgc     288
Leu Gln Met Asn Ser Leu Arg Ala Glu Asp Thr Ala Val Tyr Tyr Cys
                85                  90                  95 gct aaa gaa ggc ggt ggc tac agg gac tat ttt gat tat tgg ggc cag     336
Ala Lys Glu Gly Gly Gly Tyr Arg Asp Tyr Phe Asp Tyr Trp Gly Gln
            100                 105                 110 ggg acc ttg gtc acc gtg tcc tca gcc tcc acc aag ggc cca tcg gtc     384
Gly Thr Leu Val Thr Val Ser Ser Ala Ser Thr Lys Gly Pro Ser Val
        115                 120                 125 ttc ccc ctg gca ccc tcc tcc aag agc acc tct ggg ggc aca gcg gcc     432
Phe Pro Leu Ala Pro Ser Ser Lys Ser Thr Ser Gly Gly Thr Ala Ala
    130                 135                 140 ctg ggc tgc ctg gtc aag gac tac ttc ccc gaa ccg gtg acg gtg tcg     480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc     528
Trp Asn Ser Gly Ala Leu Thr Ser Gly Val His Thr Phe Pro Ala Val
                165                 170                 175 cta cag tcc tca gga ctc tac tcc ctt agt agc gtg gtg acc gtg ccc     576
Leu Gln Ser Ser Gly Leu Tyr Ser Leu Ser Ser Val Val Thr Val Pro
            180                 185                 190 tcc agc agc ttg ggc acc cag acc tac atc tgc aac gtg aat cac aag     624
Ser Ser Ser Leu Gly Thr Gln Thr Tyr Ile Cys Asn Val Asn His Lys
        195                 200                 205 ccc agc aac acc aag gtg gac aag aaa gtt gag ccc aaa tct tgt gac     672
Pro Ser Asn Thr Lys Val Asp Lys Lys Val Glu Pro Lys Ser Cys Asp
    210                 215                 220 aaa act cac aca tgc cca ccg tgc cca gca cct gaa ctc ctg ggg gga     720
Lys Thr His Thr Cys Pro Pro Cys Pro Ala Pro Glu Leu Leu Gly Gly
225                 230                 235                 240 ccg tca gtc ttc ctc ttc ccc cca aaa ccc aag gac acc ctc atg atc     768
Pro Ser Val Phe Leu Phe Pro Pro Lys Pro Lys Asp Thr Leu Met Ile
                245                 250                 255 tcc cgg acc cct gag gtc aca tgc gtg gtg gtg gac gtg agc cac gaa     816
Ser Arg Thr Pro Glu Val Thr Cys Val Val Val Asp Val Ser His Glu
            260                 265                 270 gac cct gag gtc aag ttc aac tgg tac gtg gac ggc gtg gag gtg cat     864
Asp Pro Glu Val Lys Phe Asn Trp Tyr Val Asp Gly Val Glu Val His
        275                 280                 285 aat gcc aag aca aag ccg cgg gag gag cag tac aac agc acg tac cgt     912
```

```
Asn Ala Lys Thr Lys Pro Arg Glu Glu Gln Tyr Asn Ser Thr Tyr Arg
    290                 295                 300 gtg gtc agc gtc ctc acc gtc ctg cac cag gac tgg ctg aat ggc aag      960
Val Val Ser Val Leu Thr Val Leu His Gln Asp Trp Leu Asn Gly Lys
305                 310                 315                 320 gag tac aag tgc aag gtc tcc aac aaa gcc ctc cca gcc ccc atc gag     1008
Glu Tyr Lys Cys Lys Val Ser Asn Lys Ala Leu Pro Ala Pro Ile Glu
                325                 330                 335 aaa acc atc tcc aaa gcc aaa ggg cag ccc cga gaa cca cag gtg tac     1056
Lys Thr Ile Ser Lys Ala Lys Gly Gln Pro Arg Glu Pro Gln Val Tyr
            340                 345                 350 acc ctg ccc cca tcc cgg gat gag ctg acc aag aac cag gtc agc ctg     1104
Thr Leu Pro Pro Ser Arg Asp Glu Leu Thr Lys Asn Gln Val Ser Leu
        355                 360                 365 acc tgc ctg gtc aaa ggc ttc tat ccc agc gac atc gcc gtg gag tgg     1152
Thr Cys Leu Val Lys Gly Phe Tyr Pro Ser Asp Ile Ala Val Glu Trp
370                 375                 380 gag agc aat ggg cag ccg gag aac aac tac aag acc acg cct ccc gtg     1200
Glu Ser Asn Gly Gln Pro Glu Asn Asn Tyr Lys Thr Thr Pro Pro Val
385                 390                 395                 400 ctg gac tcc gac ggc tcc ttc ttc ctc tac agc aag ctc acc gtg gac     1248
Leu Asp Ser Asp Gly Ser Phe Phe Leu Tyr Ser Lys Leu Thr Val Asp
                405                 410                 415 aag agc agg tgg cag cag ggg aac gtc ttc tca tgc tcc gtg atg cat     1296
Lys Ser Arg Trp Gln Gln Gly Asn Val Phe Ser Cys Ser Val Met His
            420                 425                 430 gag gct ctg cac aac cac tac acg cag aag agc ctc tcc ctg tct ccg     1344
Glu Ala Leu His Asn His Tyr Thr Gln Lys Ser Leu Ser Leu Ser Pro
        435                 440                 445 ggt aaa tga                                                         1353
Gly Lys
    450

<210> SEQ ID NO 8
<211> LENGTH: 450
<212> TYPE: PRT
<213> ORGANISM: Artificial Sequence
<220> FEATURE:
<223> OTHER INFORMATION: Heavy chain of anti-human TLR2 antibody

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ala Ala Ile Tyr Gly Arg Gly Gly Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Gly Gly Tyr Arg Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 9
<211> LENGTH: 40
<212> TYPE: PRT
<213> ORGANISM: Artificial Sequence
<220> FEATURE:
<223> OTHER INFORMATION: linker

<400> SEQUENCE: 9

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser Gly Gly Gly Gly Ser
        35                  40
```

```
<210> SEQ ID NO 10
<211> LENGTH: 15
<212> TYPE: PRT
<213> ORGANISM: Artificial Sequence
<220> FEATURE:
<223> OTHER INFORMATION: linker

<400> SEQUENCE: 10

Gly Gly Gly Gly Ser Gly Gly Gly Gly Ser Gly Gly Gly Gly Ser
1               5                  10                  15
```

BISPECIFIC ANTIBODY BINDING TO HUMAN TLR2 AND HUMAN TLR4

CROSS-REFERENCE TO RELATED APPLICATIONS

This application is a National Stage application of PCT/JP2015/055860, filed Feb. 27, 2015, which claims priority from Japanese application JP 2014-038438, filed Feb. 28, 2014.

TECHNICAL FIELD

The present invention relates to a novel bispecific antibody binding to human TLR2 and human TLR4.

BACKGROUND ART

Toll-like receptor 2 (TLR2) and Toll-like receptor 4 (TLR4) are single transmembrane proteins which are expressed in a wide spectrum of cells and tissues including immunocompetent cells such as macrophages and neutrophils, vascular endothelial cells, and renal intrinsic cells such as renal tubular epithelial cells (Folia Biol(Praha)., 2005, Vol. 51, No. 6, p. 188-197). TLR2 forms a complex with TLR1 or TLR6, and reacts with bacterial components such as peptidoglycan or lipoprotein. Meanwhile, TLR4 forms a complex with a myeloid differentiation factor 2 (MD2) protein, a CD14 protein, or the like, and reacts with bacterial components such as lipopolysaccharide typified by lipopolysaccharide (LPS). In addition, these receptors are activated by binding to damage associated molecular patterns (DAMPs) which are an endogenous tissue damage factor, and transmit signals into cells. Activation of TLR2 and TLR4 induces the expression of inflammatory cytokines such as tumor necrosis factor α (TNFα) and interleukin 6 (IL-6) and elicits an inflammatory response, for example, through the activation of a nuclear factor κB (NF-κB) which is a transcription factor (Nat. Immunol., 2010, Vol. 11, No. 5, p. 373-384).

Such TLR2- and TLR4-mediated activation of various cells is known to be involved in immune inflammatory diseases such as sepsis, acute renal failure, chronic renal disease, acute respiratory distress syndrome, scleroderma, acute pancreatitis, and chronic obstructive pulmonary disease.

In association with sepsis, it has been reported that genetically TLR2-deficient animals (knockout mice) in a *Salmonella* infection model which is a sepsis model exhibit a survival rate improvement, TLR4 knockout mice in an *Escherichia coli* infection model exhibit a survival rate improvement, and mice with a double knockout of TLR2 and TLR4 in each model exhibit a significantly improved survival rate as compared to mice with a single knockout of TLR2 or TLR4 (J. Exp. Med., 2008, Vol. 205, p. 1747-1754). In addition, it has been reported that the survival rate is not improved with administration of an anti-TLR2 antibody (T2.5) or an anti-TLR4 antibody (1A6) alone in the above two models, whereas the survival rate is improved with combined administration of both antibodies (J. Exp. Med., 2008, Vol. 205, p. 1747-1754).

In association with acute pancreatitis, it has been reported that TLR4 knockout mice in a taurocholate-induced pancreatitis model exhibit lowering of blood amylase, pancreatic myeloperoxidase, and pancreatic tissue damage (Inflamm. Res., 2011, Vol. 60, p. 1093-1098). Further, it has been reported that the expression level of TLR2 and TLR4 in the pancreas is increased in a caerulein-induced pancreatitis model (Pancreas, 2013, Vol. 42, p. 114-122).

As an antibody binding to human TLR2, a mouse monoclonal antibody T2.5 (Patent Document 1), a mouse monoclonal antibody 11G7 (Patent Document 2), and a humanized monoclonal antibody OPN305 (Patent Document 3) of T2.5 have been reported. Among them, 11G7 inhibits TLR2/TLR1 signals but does not inhibit TLR2/TLR6 signals, whereas OPN305 has been reported to inhibit both signals. Specifically, it has been reported that in experiments using a THP-1 cell which is a human monocytic cell, OPN305 has a neutralizing activity against both Pam3CSK4 (TLR2/TLR1 agonist) stimulation and FSL-1 (TLR2/TLR6 agonist) stimulation, and inhibits the elevation of a mouse serum inflammatory cytokine concentration induced by administration of Pam3CSK4 (Patent Document 3).

As an antibody binding to human TLR4, a mouse monoclonal antibody HTA125 (Non-Patent Document 1), mouse monoclonal antibodies 18H10, 16G7, 15C1 and 7E3 (Patent Document 4), a humanized monoclonal antibody hu15C1 of 15C1 (Patent Document 5), and humanized monoclonal antibodies 1A6 and 1E11.C2E3 and the like discovered by random mutations to the complementarity determining region of hu15C1 (Patent Document 6) have been reported. Among them, with respect to mouse monoclonal antibodies, 15C1 has been shown to have the highest neutralizing activity from the experimental results using human blood (Patent Document 4), and the humanized monoclonal antibody hu15C1 of 15C1 has been confirmed to have a neutralizing activity by experiments using the same human blood (Patent Document 5). Further, the humanized monoclonal antibody 1E11.C2E3 has been reported to have a superior neutralizing activity than hu15C1 in experiments using human blood (Patent Document 6).

In addition, it has been reported that, in an IL-6 production evaluation system for stimulation of *Escherichia coli, Pseudomonas* and *Klebsiella* subjected to a heat treatment using human blood, the anti-human TLR2 antibody (T2.5) weakly inhibits IL-6 production and the anti-human TLR4 antibody (15C1) inhibits about 50% of IL-6 production, whereas the combined addition of both antibodies almost completely inhibits IL-6 production (Patent Document 7).

However, a bispecific antibody binding to human TLR2 and human TLR4 has not been reported thus far.

RELATED ART

Patent Document

Patent Document 1: WO 2005/028509
Patent Document 2: WO 2005/019431
Patent Document 3: WO 2011/003925
Patent Document 4: WO 2005/065015
Patent Document 5: WO 2007/110678
Patent Document 6: WO 2013/149111
Patent Document 7: WO 2006/077471

Non-Patent Document

Non-Patent Document 1: "The Journal of Experimental Medicine", (US), 1999, Vol. 189, No. 11, p. 1777-1782

DISCLOSURE OF INVENTION

Problems to be Solved by the Invention

An object of the present invention is to provide a bispecific antibody for preventing or treating an immune inflammatory disease by binding to both human TLR2 and human TLR4 to inhibit human TLR2- and human TLR4-mediated immune inflammatory effects.

Means for Solving the Problems

The present inventors have extensively and repeatedly conducted inventive studies on the preparation of a bispecific antibody binding to human TLR2 and human TLR4. As a consequence, the present inventors have prepared a bispecific antibody binding to human TLR2 and human TLR4, comprising 1) a heavy chain variable region of an anti-human TLR2 antibody consisting of the amino acid sequence of amino acid numbers 1 to 120 of SEQ ID NO: 4, and a light chain variable region of an anti-human TLR2 antibody consisting of the amino acid sequence of amino acid numbers 1 to 113 of SEQ ID NO: 6; and 2) a heavy chain variable region of an anti-human TLR4 antibody consisting of the amino acid sequence of amino acid numbers 491 to 609 of SEQ ID NO: 4, and a light chain variable region of an anti-human TLR4 antibody consisting of the amino acid sequence of amino acid numbers 625 to 732 of SEQ ID NO: 4 (Examples 1 to 8), and have found that the bispecific antibody inhibits the production of TNFα which is a proinflammatory cytokine induced by a heat-killed bacterium of clinical isolate-derived *Pseudomonas aeruginosa* PAO-1 (hereinafter referred to as a killed bacterium) responding to TLR2 and TLR4 (Example 10). The bispecific antibody binding to human TLR2 and human TLR4 has been provided and the present invention has been completed based on these results. Further, the present inventors have found that the bispecific antibody also inhibits the production of TNFα induced by a killed bacterium of clinical isolate-derived *Escherichia coli* 21006 (Example 11).

That is, the present invention includes the following invention as a material or a method which is medically or industrially applicable.

[i] A bispecific antibody binding to human TLR2 and human TLR4, which is selected from the following (1) or (2):

(1) a bispecific antibody binding to human TLR2 and human TLR4, comprising 1) a heavy chain variable region of an anti-human TLR2 antibody consisting of the amino acid sequence of amino acid numbers 1 to 120 of SEQ ID NO: 4, and a light chain variable region of an anti-human TLR2 antibody consisting of the amino acid sequence of amino acid numbers 1 to 113 of SEQ ID NO: 6, and 2) a heavy chain variable region of an anti-human TLR4 antibody consisting of the amino acid sequence of amino acid numbers 491 to 609 of SEQ ID NO: 4, and a light chain variable region of an anti-human TLR4 antibody consisting of the amino acid sequence of amino acid numbers 625 to 732 of SEQ ID NO: 4; or (2) a bispecific antibody binding to human TLR2 and human TLR4, which is a bispecific antibody derived from post-translational modification of the bispecific antibody of (1).

[ii] The bispecific antibody according to [i], which is selected from the following (1) or (2):

(1) a bispecific antibody comprising an anti-human TLR2 antibody and an anti-human TLR4 antibody fragment, wherein the anti-human TLR2 antibody is an IgG antibody and comprises a heavy chain variable region of an anti-human TLR2 antibody consisting of the amino acid sequence of amino acid numbers 1 to 120 of SEQ ID NO: 4, and a light chain variable region of an anti-human TLR2 antibody consisting of the amino acid sequence of amino acid numbers 1 to 113 of SEQ ID NO: 6, and the anti-human TLR4 antibody fragment is a single chain variable region fragment (scFv) and comprises a heavy chain variable region of an anti-human TLR4 antibody consisting of the amino acid sequence of amino acid numbers 491 to 609 of SEQ ID NO: 4, and a light chain variable region of an anti-human TLR4 antibody consisting of the amino acid sequence of amino acid numbers 625 to 732 of SEQ ID NO: 4; or (2) a bispecific antibody binding to human TLR2 and human TLR4, which is a bispecific antibody derived from post-translational modification of the bispecific antibody of (1).

[iii] The bispecific antibody according to [ii], wherein the bispecific antibody comprises an anti-human TLR2 antibody and an anti-human TLR4 antibody fragment, the anti-human TLR2 antibody is an IgG antibody and comprises a heavy chain variable region of an anti-human TLR2 antibody consisting of the amino acid sequence of amino acid numbers 1 to 120 of SEQ ID NO: 4, and a light chain variable region of an anti-human TLR2 antibody consisting of the amino acid sequence of amino acid numbers 1 to 113 of SEQ ID NO: 6, and the anti-human TLR4 antibody fragment is an scFv and comprises a heavy chain variable region of an anti-human TLR4 antibody consisting of the amino acid sequence of amino acid numbers 491 to 609 of SEQ ID NO: 4, and a light chain variable region of an anti-human TLR4 antibody consisting of the amino acid sequence of amino acid numbers 625 to 732 of SEQ ID NO: 4.

[iv] The bispecific antibody according to [ii], wherein the post-translational modification is pyroglutamylation at the amino terminal (N terminal) of the heavy chain variable region of the anti-human TLR2 antibody, deletion of lysine at the heavy chain carboxy terminal (C terminal) of the anti-human TLR2 antibody, and/or pyroglutamylation at the N terminal of the heavy chain variable region of the anti-human TLR4 antibody fragment.

[v] The bispecific antibody according to any one of [ii] to [iv], wherein the anti-human TLR2 antibody comprises a heavy chain constant region which is a human Igγ1 constant region.

[vi] The bispecific antibody according to [v], wherein the human Igγ1 constant region is a human Igγ1 constant region having amino acid mutations of L234A and L235A or amino acid mutations of L234A, L235A and I253A.

[vii] The bispecific antibody according to any one of [ii] to [iv], wherein the anti-human TLR2 antibody comprises a light chain constant region which is a human Igκ constant region.

[viii] The bispecific antibody according to any one of [ii] to [iv], wherein the anti-human TLR2 antibody comprises a heavy chain constant region which is a human Igγ1 constant region and a light chain constant region which is a human Igκ constant region.

[ix] The bispecific antibody according to [viii], wherein the human Igγ1 constant region is a human Igγ1 constant region having amino acid mutations of L234A and L235A or amino acid mutations of L234A, L235A and I253A.

[x] The bispecific antibody according to [ii] or [iii], wherein the anti-human TLR2 antibody comprises a heavy chain consisting of the amino acid sequence of amino acid numbers 1 to 450 of SEQ ID NO: 4 and a light chain consisting of the amino acid sequence of SEQ ID NO: 6.

[xi] The bispecific antibody according to any one of [ii] to [x], wherein the anti-human TLR4 antibody fragment is an scFv having a structure where the N terminal of the light chain variable region is connected via a linker to the C terminal of the heavy chain variable region.

[xii] The bispecific antibody according to any one of [ii] to [xi], wherein the anti-human TLR4 antibody fragment is an scFv consisting of the amino acid sequence of amino acid numbers 491 to 732 of SEQ ID NO: 4.

[xiii] The bispecific antibody according to [ii] or [iii], wherein the anti-human TLR2 antibody comprises a heavy chain consisting of the amino acid sequence of amino acid numbers 1 to 450 of SEQ ID NO: 4 and a light chain consisting of the amino acid sequence of SEQ ID NO: 6, and the anti-human TLR4 antibody fragment is an scFv consisting of the amino acid sequence of amino acid numbers 491 to 732 of SEQ ID NO: 4.

[xiv] The bispecific antibody according to any one of [ii] to [xiii], wherein the N terminal of the anti-human TLR4 antibody fragment is connected via a linker to the C terminal of each heavy chain of the anti-human TLR2 antibody.

[xv] The bispecific antibody according to [xiv], wherein the linker connecting the heavy chain of the anti-human TLR2 antibody and the anti-human TLR4 antibody fragment consists of a GS linker.

[xvi] The bispecific antibody according to [xv], wherein the GS linker consists of the amino acid sequence of SEQ ID NO: 9.

[xvii] The bispecific antibody according to [ii] or [iii], wherein the anti-human TLR2 antibody comprises a heavy chain consisting of the amino acid sequence of amino acid numbers 1 to 450 of SEQ ID NO: 4 and a light chain consisting of the amino acid sequence of SEQ ID NO: 6, the anti-human TLR4 antibody fragment is an scFv consisting of the amino acid sequence of amino acid numbers 491 to 732 of SEQ ID NO: 4, and the N terminal of the anti-human TLR4 antibody fragment is connected via a linker to the C terminal of each heavy chain of the anti-human TLR2 antibody.

[xviii] The bispecific antibody according to [xvii], wherein the linker connecting the heavy chain of the anti-human TLR2 antibody and the anti-human TLR4 antibody fragment consists of a GS linker.

[xix] The bispecific antibody according [xviii], wherein the GS linker consists of the amino acid sequence of SEQ ID NO: 9.

[xx] A bispecific antibody derived from post-translational modification of the bispecific antibody according to any one of [xvii] to [xix].

[xxi] A polynucleotide comprising a base sequence encoding the heavy chain variable region of the anti-human TLR2 antibody, the light chain variable region of the anti-human TLR2 antibody, the heavy chain variable region of the anti-human TLR4 antibody and/or the light chain variable region of the anti-human TLR4 antibody of the bispecific antibody according to [i].

[xxii] A polynucleotide comprising a base sequence encoding a fusion where the N terminal of the anti-human TLR4 antibody fragment is connected via a linker to the C terminal of the heavy chain of the anti-human TLR2 antibody of the bispecific antibody according to any one of [xvii] to [xix].

[xxiii] The polynucleotide according to [xxii], comprising a base sequence encoding the fusion consisting of the amino acid sequence of SEQ ID NO: 4.

[xxiv] A polynucleotide comprising a base sequence encoding the light chain of the anti-human TLR2 antibody of the bispecific antibody according to any one of [xvii] to [xix].

[xxv] An expression vector comprising the polynucleotide according to [xxi].

[xxvi] An expression vector comprising the polynucleotide according to [xxii], [xxiii] and/or [xxiv].

[xxvii] A host cell transformed with the expression vector according to [xxv], selected from the group consisting of the following (a) to (d):
  (a) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4, and an expression vector comprising a polynucleotide comprising a base sequence encoding a light chain variable region of an anti-human TLR2 antibody consisting of the amino acid sequence of amino acid numbers 1 to 113 of SEQ ID NO: 6;
  (b) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, a polynucleotide comprising a base sequence encoding a light chain variable region of an anti-human TLR4 antibody consisting of the amino acid sequence of amino acid numbers 625 to 732 of SEQ ID NO: 4, and a polynucleotide comprising a base sequence encoding a light chain variable region of an anti-human TLR2 antibody consisting of the amino acid sequence of amino acid numbers 1 to 113 of SEQ ID NO: 6;
  (c) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4; and
  (d) a host cell transformed with an expression vector comprising a polynucleotide comprising a base sequence encoding a light chain variable region of an anti-human TLR2 antibody consisting of the amino acid sequence of amino acid numbers 1 to 113 of SEQ ID NO: 6.

[xxviii] A host cell transformed with the expression vector according to [xxv], selected from the group consisting of the following (a) to (d):
  (a) a host cell transformed with an expression vector comprising the polynucleotide according to [xxii] or [xxiii] and an expression vector comprising the polynucleotide according to [xxiv];
  (b) a host cell transformed with an expression vector comprising the polynucleotide according to [xxii] or [xxiii] and the polynucleotide according to [xxiv];

(c) a host cell transformed with an expression vector comprising the polynucleotide according to [xxii] or [xxiii]; and (d) a host cell transformed with an expression vector comprising the polynucleotide according to claim [xxiv].

[xxix] A method for producing a bispecific antibody binding to human TLR2 and human TLR4, comprising culturing host cell(s) selected from the group consisting of the following (a) to (c) to express the bispecific antibody binding to human TLR2 and human TLR4:

(a) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4, and an expression vector comprising a polynucleotide comprising a base sequence encoding a light chain variable region of an anti-human TLR2 antibody consisting of the amino acid sequence of amino acid numbers 1 to 113 of SEQ ID NO: 6;

(b) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, a polynucleotide comprising a base sequence encoding a light chain variable region of an anti-human TLR4 antibody consisting of the amino acid sequence of amino acid numbers 625 to 732 of SEQ ID NO: 4, and a polynucleotide comprising a base sequence encoding a light chain variable region of an anti-human TLR2 antibody consisting of the amino acid sequence of amino acid numbers 1 to 113 of SEQ ID NO: 6; and (c) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4, and a host cell transformed with an expression vector comprising a polynucleotide comprising a base sequence encoding a light chain variable region of an anti-human TLR2 antibody consisting of the amino acid sequence of amino acid numbers 1 to 113 of SEQ ID NO: 6.

[xxx] A method for producing a bispecific antibody binding to anti-human TLR2 and human TLR4, comprising culturing host cell(s) selected from the group consisting of the following (a) to (c) to express a bispecific antibody binding to human TLR2 and human TLR4:

(a) a host cell transformed with an expression vector comprising the polynucleotide according to [xxii] or [xxiii] and an expression vector comprising the polynucleotide according to [xxiv];

(b) a host cell transformed with an expression vector comprising the polynucleotide according to [xxii] or [xxiii] and the polynucleotide according to [xxiv]; and (c) a host cell transformed with an expression vector comprising the polynucleotide according to [xxii] or [xxiii], and a host cell transformed with an expression vector comprising the polynucleotide according to [xxiv].

[xxxi] A bispecific antibody binding to human TLR2 and human TLR4, produced by the method according to [xxii].

[xxiii] A bispecific antibody binding to human TLR2 and human TLR4, produced by the method according to [xxx].

[xxxiii] A pharmaceutical composition comprising the bispecific antibody according to any one of [i] to [xx], [xxxi] and [xxxii], and a pharmaceutically acceptable excipient.

[xxxiv] The pharmaceutical composition according to [xxxiii], which is a pharmaceutical composition for preventing or treating an immune inflammatory disease.

[xxxv] The pharmaceutical composition according to [xxxiv], wherein the immune inflammatory disease is sepsis or acute pancreatitis.

[xxxvi] A method for preventing or treating an immune inflammatory disease, comprising administering a therapeutically effective amount of the bispecific antibody according to any one of [i] to [xx], [xxxi] and [xxiii].

[xxxvii] The method for preventing or treating according to [xxxvi], wherein the immune inflammatory disease is sepsis or acute pancreatitis.

[xxxviii] The bispecific antibody according to any one of [i] to [xx], [xxxi] and [xxiii] for use in preventing or treating an immune inflammatory disease.

[xxxix] The bispecific antibody according to [xxxviii], wherein the immune inflammatory disease is sepsis or acute pancreatitis.

[xl] Use of the bispecific antibody according to any one of [i] to [xx], [xxxi] and [xxiii] in the manufacture of a pharmaceutical composition for preventing or treating an immune inflammatory disease.

[xli] The use of the bispecific antibody according to [xl], wherein the immune inflammatory disease is sepsis or acute pancreatitis.

[xlii] A bispecific antibody binding to human TLR2 and human TLR4, comprising:

1) a heavy chain variable region of an anti-human TLR2 antibody comprising CDR1 consisting of the amino acid sequence of amino acid numbers 31 to 35 of SEQ ID NO: 4, CDR2 consisting of the amino acid sequence of amino acid numbers 50 to 66 of SEQ ID NO: 4 and CDR3 consisting of the amino acid sequence of amino acid numbers 99 to 109 of SEQ ID NO: 4, and a light chain variable region of an anti-human TLR2 antibody comprising CDR1 consisting of the amino acid sequence of amino acid numbers 24 to 39 of SEQ ID NO: 6, CDR2 consisting of the amino acid sequence of amino acid numbers 55 to 61 of SEQ ID NO: 6 and CDR3 consisting of the amino acid sequence of amino acid numbers 94 to 102 of SEQ ID NO: 6; and 2) a heavy chain variable region of an anti-human TLR4 antibody comprising CDR1 consisting of the amino acid sequence of amino acid numbers 521 to 525 of SEQ ID NO: 4, CDR2 consisting of the amino acid sequence of amino acid numbers 540 to 556 of SEQ ID NO: 4 and CDR3 consisting of the amino acid sequence of amino acid numbers 589 to 598 of SEQ ID NO: 4, and a light chain variable region of an anti-human TLR4 antibody comprising CDR1 consisting of the amino acid sequence of amino acid numbers 648 to 658 of SEQ ID NO: 4, CDR2 consisting of the amino acid sequence of amino acid numbers 674 to 680 of SEQ ID NO: 4 and CDR3 consisting of the amino acid sequence of amino acid numbers 713 to 721 of SEQ ID NO: 4.

[xliii] The anti-human TLR2 antibody or the antigen-binding fragment thereof according to [xlii], comprising a heavy chain variable region consisting of the amino acid sequence of amino acid numbers 1 to 120 of SEQ ID NO: 8 and a light chain variable region consisting of the amino acid sequence of amino acid numbers 1 to 113 of SEQ ID NO: 6.

[xliv] The anti-human TLR2 antibody or the antigen-binding fragment thereof according to [xlii], which is an antibody or an antigen-binding fragment thereof derived from post-translational modification of an anti-human TLR2 antibody or an antigen-binding fragment thereof comprising a heavy chain variable region consisting of the amino acid sequence of amino acid numbers 1 to 120 of SEQ ID NO: 8 and a light chain variable region consisting of the amino acid sequence of amino acid numbers 1 to 113 of SEQ ID NO: 6.

[xlv] The anti-human TLR2 antibody or the antigen-binding fragment thereof according to [xlii] or [xliv], wherein the post-translational modification is pyroglutamylation at the N terminal of the heavy chain variable region and/or deletion of lysine at the C terminal of the heavy chain.

[xlvi] The anti-human TLR2 antibody or the antigen-binding fragment thereof according to any one of [xlii] to [xlv], comprising a heavy chain constant region which is a human Igγ1 constant region.

[xlvii] The anti-human TLR2 antibody or the antigen-binding fragment thereof according to [xlvi], wherein the human Igγ1 constant region is a human Igγ1 constant region having amino acid mutations of L234A and L235A or amino acid mutations of L234A, L235A and I253A.

[xlviii] The anti-human TLR2 antibody or the antigen-binding fragment thereof according to any one of [xlii] to [xlv], comprising a light chain constant region which is a human Igκ constant region.

[xlix] The anti-human TLR2 antibody or the antigen-binding fragment thereof according to any one of [xlii] to [xliv], comprising a heavy chain constant region which is a human Igγ1 constant region and a light chain constant region which is a human Igκ constant region.

[l] The anti-human TLR2 antibody or the antigen-binding fragment thereof according to [xlix], wherein the human Igγ1 constant region is a human Igγ1 constant region having amino acid mutations of L234A and L235A or amino acid mutations of L234A, L235A and I253A.

[li] The anti-human TLR2 antibody according to [xlii] or [xliii], comprising a heavy chain consisting of the amino acid sequence of amino acid numbers 1 to 450 of SEQ ID NO: 8 and a light chain consisting of the amino acid sequence of SEQ ID NO: 6.

[lii] The antigen-binding fragment according to any one of [xlii] to [li], which is a single chain variable region fragment, Fab, Fab', or F(ab')2.

[liii] An anti-human TLR2 antibody which is an antibody derived from post-translational modification of the anti-human TLR2 antibody according to [li].

[liv] The anti-human TLR2 antibody according to [liii], wherein the post-translational modification is pyroglutamylation at the N terminal of the heavy chain variable region and/or deletion of lysine at the C terminal of the heavy chain.

[lv] The anti-human TLR2 antibody according to [xlii] to [xliv], comprising a heavy chain consisting of the amino acid sequence of amino acid numbers 1 to 449 of SEQ ID NO: 8 and a light chain consisting of the amino acid sequence of SEQ ID NO: 6.

[lvi] A method for producing an anti-human TLR2 antibody or an antigen-binding fragment thereof, comprising culturing host cell(s) selected from the group consisting of the following (a) to (c) to express the anti-human TLR2 antibody or the antigen-binding fragment thereof:

(a) a host cell transformed with an expression vector comprising a polynucleotide comprising a base sequence encoding a heavy chain variable region of the anti-human TLR2 antibody or the antigen-binding fragment thereof according to [xliii], and a polynucleotide comprising a base sequence encoding a light chain variable region of the anti-human TLR2 antibody or the antigen-binding fragment thereof according to [xliii];

(b) a host cell transformed with an expression vector comprising a polynucleotide comprising a base sequence encoding a heavy chain variable region of the anti-human TLR2 antibody or the antigen-binding fragment thereof according to [xliii], and an expression vector comprising a polynucleotide comprising a base sequence encoding a light chain variable region of the anti-human TLR2 antibody or the antigen-binding fragment thereof according to [xliii]; and (c) a host cell transformed with an expression vector comprising a polynucleotide comprising a base sequence encoding a heavy chain variable region of the anti-human TLR2 antibody or the antigen-binding fragment thereof according to [xliii], and a host cell transformed with an expression vector comprising a polynucleotide comprising a base sequence encoding a light chain variable region of the anti-human TLR2 antibody or the antigen-binding fragment thereof according to [xliii].

[lvii] A method for producing an anti-human TLR2 antibody, comprising culturing host cell(s) selected from the group consisting of the following (a) to (c) to express the anti-human TLR2 antibody:

(a) a host cell transformed with an expression vector comprising a polynucleotide comprising a base sequence encoding a heavy chain of the anti-human TLR2 antibody according to [li], and a polynucleotide comprising a base sequence encoding a light chain of the anti-human TLR2 antibody according to [li];

(b) a host cell transformed with an expression vector comprising a polynucleotide comprising a base sequence encoding a heavy chain of the anti-human TLR2 antibody according to [li], and an expression vector comprising a polynucleotide comprising a base sequence encoding a light chain of the anti-human TLR2 antibody according to [li]; and (c) a host cell transformed with an expression vector comprising a polynucleotide comprising a base sequence encoding a heavy chain of the anti-human TLR2 antibody according to [li], and a host cell transformed with an expression vector comprising a polynucleotide comprising a base sequence encoding a light chain of the anti-human TLR2 antibody according to [li].

[lviii] An anti-human TLR2 antibody or an antigen-binding fragment thereof produced by the method according to [lvi].

[lix] An anti-human TLR2 antibody produced by the method according to [lvii].

[lx] A pharmaceutical composition comprising the anti-human TLR2 antibody or the antigen-binding fragment thereof according to any one of [xlii] to [lv], [lviii] and [lix], and a pharmaceutically acceptable excipient.

[lxi] A pharmaceutical composition comprising the anti-human TLR2 antibody or the antigen-binding fragment thereof according to [xliii], the anti-human TLR2 antibody or the antigen-binding fragment thereof according to [xliv], and a pharmaceutically acceptable excipient.
[lxii] A pharmaceutical composition comprising the anti-human TLR2 antibody according to [li], the anti-human TLR2 antibody according to [lv], and a pharmaceutically acceptable excipient.
[lxiii] The pharmaceutical composition according to any one of [lx] to [lxii], which is a pharmaceutical composition for preventing or treating cancer.
[lxiv] A method for preventing or treating cancer, comprising administering a therapeutically effective amount of the anti-human TLR2 antibody or the antigen-binding fragment thereof according to any one of [xlii] to [lv], [lviii] and [lix].
[lxv] The anti-human TLR2 antibody or the antigen-binding fragment thereof according to any one of [xlii] to [lv], [lviii] and [lix] for use in preventing or treating cancer.
[lxvi] Use of the anti-human TLR2 or the antigen-binding fragment thereof according to any one of [xlii] to [lv], [lviii] and [lix] in the manufacture of a pharmaceutical composition for preventing or treating cancer.

The bispecific antibody binding to human TLR2 and human TLR4 and the anti-human TLR2 antibody and the antigen-binding fragments thereof also include a fusion of the antibody or the antigen-binding fragment thereof with another peptide or protein, and a modification having a modifying agent bound thereto.

Effects of the Invention

A bispecific antibody of the present invention has a potent anti-immune inflammatory activity by functional inhibition of human TLR2 and human TLR4 and can be used as an agent for preventing or treating an immune inflammatory disease.

EMBODIMENTS FOR CARRYING OUT THE INVENTION

Figure 1:
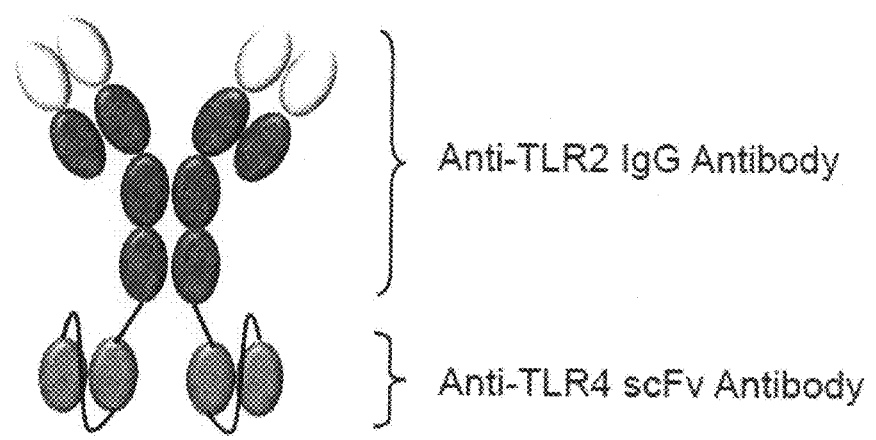
FIG. 1 shows an example of a structure of a bispecific antibody of the present invention in which the N terminal of an anti-human TLR4 antibody scFv is connected via a linker to the C terminal of each heavy chain of an anti-human TLR2 antibody which is an IgG antibody.

Hereinafter, the present invention will be described in detail.

There are five classes of IgG, IgM, IgA, IgD, and IgE in an antibody. The basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, Igδ, and Igε corresponding to IgG IgM, IgA, IgD, and IgE, respectively. Further, four subclasses of IgG1, IgG2, IgG3, and IgG4 are present in IgG; and the heavy chains respectively corresponding thereto are referred to as Igγ1, Igγ2, Igγ3, and Igγ4. Light chain usually consists of a polypeptide chain comprising approximately 220 amino acids, two types of which, type L and type K are known, and are referred to as Igλ and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain. The respective antibody molecules typically consist of two identical light chains and two identical heavy chains.

With regard to intrachain S—S bonds, four of the S—S bonds are present in the heavy chain (five in Igμ and Igε) and two of them are present in the light chain; one loop is formed per 100 to 110 amino acid residues, and this steric structure is similar among the loops and are referred to as a structural unit or a domain. The domain located at the N terminal side in both of the heavy chain and the light chain, whose amino acid sequence is not constant even in a case of a sample from the same class (subclass) of the same kind of animal is referred to as a variable region, and respective domains are referred to as a heavy chain variable region ($V_H$) and a light chain variable region ($V_L$). The amino acid sequence of the C terminal side from the variable region is nearly constant in each class or subclass and is referred to as a constant region (each of the domains is called $C_H1$, $C_H2$, $C_H3$ and CL, respectively).

An antigenic determinant site of an antibody is configured of $V_H$ and $V_L$, and the binding specificity depends on the amino acid sequence of this site. On the other hand, biological activities such as binding to complements and various cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

Further, various kinds of antibody fragments comprising $V_H$ and $V_L$ of an antibody also have an antigen-binding activity. Examples of typical antibody fragments include a single chain variable region fragment (scFv), Fab, Fab', and F(ab')$_2$. A Fab is a monovalent antibody fragment which is constituted of a light-chain and a heavy-chain fragment including a $V_H$ domain, a $C_H1$ domain, and a portion of the hinge region. A Fab' is a monovalent antibody fragment which is constituted of a light-chain and a heavy-chain fragment including a $V_H$ domain, a $C_H1$ domain, and a portion of the hinge region, and cysteine residues constituting the inter-heavy-chain S—S bond are included in the portion of the hinge region. An F(ab')2 fragment is a bivalent antibody fragment in which two Fab' fragments bind to each other via the inter-heavy-chain S—S bond in the hinge region. An scFv is a monovalent antibody fragment which is constituted of a $V_H$ and $V_L$ connected with a linker (for example, a peptide linker).

A bispecific antibody is an antibody comprising heavy chain variable regions and light chain variable regions of two antibodies which recognize two different antigens and bind to each antigen. With regard to the bispecific antibody, various formats (structures) have been reported (Expert Rev. Clin. Pharmacol., 2010, Vol. 3, No. 4, p. 491-508). For example, a tetravalent bispecific antibody in which the C terminals of the heavy chain variable region and light chain variable region of the other antibody are respectively connected via linkers to the N terminals of the heavy chain variable region and light chain variable region of one antibody, a bivalent bispecific antibody in which the heavy chain and light chain of each antibody are joined via CH3 by a knobs-into-holes technology, and a tetravalent bispecific antibody in which the C terminal of the other antibody scFv is connected via a linker to the N terminal of the heavy chain or light chain of one antibody, or the N terminal of the other antibody scFv is connected via a linker to the C terminal of the heavy chain or light chain of one antibody (Nature Biotech., 1997, Vol. 15, p. 159-163) have been reported.

<Bispecific Antibody of the Present Invention>

The term "bispecific antibody binding to human TLR2 and human TLR4" as used herein refers to a bispecific antibody having a binding activity to human TLR2 and a binding activity to human TLR4. Specifically, the bispecific antibody of the present invention includes a bispecific antibody having the following characteristics:

A bispecific antibody binding to human TLR2 and human TLR4, comprising:

1) a heavy chain variable region of an anti-human TLR2 antibody consisting of the amino acid sequence of amino acid numbers 1 to 120 of SEQ ID NO: 4, and a light chain variable region of an anti-human TLR2 antibody consisting of the amino acid sequence of amino acid numbers 1 to 113 of SEQ ID NO: 6; and 2) a heavy chain variable region of an anti-human TLR4 antibody consisting of the amino acid sequence of amino acid numbers 491 to 609 of SEQ ID NO: 4, and a light chain variable region of an anti-human TLR4 antibody consisting of the amino acid sequence of amino acid numbers 625 to 732 of SEQ ID NO: 4.

As used herein, the term "anti-human TLR2 antibody" refers to an antibody that binds to human TLR2, and the term "anti-human TLR4 antibody" refers to an antibody that binds to human TLR4. The bispecific antibody of the present invention may have heavy chain variable regions and light chain variable regions of each of the anti-human TLR2 antibody and anti-human TLR4 antibody, for example, may have a structure of any bispecific antibody comprising an anti-human TLR2 antibody fragment having a binding activity to an anti-human TLR2 antibody or human TLR2, and an anti-human TLR4 antibody fragment having a binding activity to an anti-human TLR4 antibody or human TLR4. Examples of such a structure include a bispecific antibody (DVD-Ig) in which the C terminals of the heavy chain variable region and light chain variable region of the other antibody are respectively connected via linkers to the N terminals of the heavy chain variable region and light chain variable region of one antibody, a bispecific antibody in which the heavy chain and light chain of each antibody are joined via CH3 by a knobs-into-holes technology, and a tetravalent bispecific antibody in which the C terminal of the other antibody scFv is connected via a linker to the N terminal of the heavy chain or light chain of one antibody, or the N terminal of the other antibody scFv is connected via a linker to the C terminal of the heavy chain or light chain of one antibody.

Preferably, the bispecific antibody of the present invention is a tetravalent bispecific antibody comprising an anti-human TLR2 antibody and an anti-human TLR4 antibody fragment wherein the anti-human TLR2 antibody is an IgG antibody, and the anti-human TLR4 antibody fragment is an scFv. Hereinafter, the tetravalent bispecific antibody having this structure is also referred to as IgG(TLR2)-scFv(TLR4).

In the case where the bispecific antibody of the present invention is an IgG(TLR2)-scFv(TLR4), constant regions of any subclass (for example, constant regions of Igγ1, Igγ2, Igγ3 or Igγ4 as the heavy chain, and Igλ or Igκ as the light chain) may be selectable as the constant region of the anti-human TLR2 antibody, but a human Igγ1 constant region is preferred as the heavy chain constant region and a human Igκ constant region is preferred as the light chain constant region.

The human Igγ1 constant region used as the heavy chain constant region of the anti-human TLR2 antibody may be, for example an amino acid sequence consisting of amino acid numbers 121 to 450 of SEQ ID NO: 8.

In the case of using a human Igγ1 constant region as the heavy chain constant region of an anti-human TLR2 antibody, a human Igγ1 constant region with the introduction of an amino acid mutation such as L234A (substitution of leucine to alanine at the amino acid position 234 in accordance with the EU index of Kabat et al.) or L235A (substitution of leucine to alanine at the amino acid position 235 in accordance with the EU index of Kabat et al.) may also be used in order to reduce the antibody-dependent cellular cytotoxicity and complement-dependent cytotoxic activity of the antibody (Mol. Immunol., 1992, Vol. 29, No. 5, p. 633-639). From the viewpoint of in vivo pharmacokinetics, a human Igγ1 constant region with the introduction of an amino acid mutation such as I253A (substitution of isoleucine to alanine at the amino acid position 253 in accordance with the EU index of Kabat et al.) may also be used in order to quickly clear the antibodies from the blood (J. Immunol., 1997, Vol. 158, p. 2211-2217). The residue numbering in the context of the introduction of an amino acid mutation into a constant region of an antibody used in this specification is according to the EU index (Kabat et al., 1991, Sequences of Proteins of Immunological Interest, 5th Ed., United States Public Health Service, National Institute of Health, Bethesda).

Preferably, the heavy chain constant region of the anti-human TLR2 antibody is a human Igγ1 constant region having amino acid mutations of L234A and L235A or a human Igγ1 constant region having amino acid mutations of L234A, L235A, and I253A. More preferably, the heavy chain constant region of the anti-human TLR2 antibody is a human Igγ1 constant region having amino acid mutations of L234A, L235A, and I253A, and such a human Igγ1 constant region may be, for example, an amino acid sequence consisting of amino acid numbers 121 to 450 of SEQ ID NO: 4.

The human Igκ constant region used as the light chain constant region of the anti-human TLR2 antibody may be, for example, an amino acid sequence consisting of amino acid numbers 114 to 219 of SEQ ID NO: 6.

Preferably, the anti-human TLR2 antibody is an anti-human TLR2 antibody comprising a heavy chain constant region which is a human Igγ1 constant region and a light chain constant region which is a human Igκ constant region, and more preferably the human Igγ1 constant region is a human Igγ1 constant region having amino acid mutations of L234A, L235A, and I253A.

For example, the anti-human TLR2 antibody may be an anti-human TLR2 antibody comprising a heavy chain consisting of the amino acid sequence of amino acid numbers 1 to 450 of SEQ ID NO: 4, and a light chain consisting of the amino acid sequence of SEQ ID NO: 6.

In the case where the bispecific antibody of the present invention is an IgG(TLR2)-scFv(TLR4), the anti-human TLR4 antibody fragment may be any one of an scFv having a structure in which the N terminal of the light chain variable region is connected via a linker to the C terminal of the heavy chain variable region (heavy chain variable region-linker-light chain variable region), and an scFv having a structure in which the N terminal of the heavy chain variable region is connected via a linker to the C terminal of the light chain variable region (light chain variable region-linker-heavy chain variable region), and is preferably an scFv having a structure of heavy chain variable region-linker-light chain variable region. The "linker" in the scFv is a peptide (peptide linker) of any length connecting the heavy chain variable region and the light chain variable region. The peptide linker is a peptide preferably having at least 5 amino acids, more preferably at least 10 amino acids, and still more preferably 15 to 50 amino acids. The preferred peptide linker is a peptide linker comprising the amino acid sequence GlyGlyGlyGlySer (also denoted as (Gly)$_4$Ser) (referred to herein as "GS linker"), preferably a plurality of (Gly)$_4$Ser, and more preferably three to five (Gly)$_4$Ser.

For example, the anti-human TLR4 antibody fragment may be an anti-human TLR4 antibody fragment which is an scFv consisting of the amino acid sequence of amino acid numbers 491 to 732 of SEQ ID NO: 4.

In one embodiment, the bispecific antibody of the present invention which is an IgG(TLR2)-scFv(TLR4) is a bispecific antibody wherein the anti-human TLR2 antibody comprises a heavy chain consisting of the amino acid sequence of amino acid numbers 1 to 450 of SEQ ID NO: 4, and a light chain consisting of the amino acid sequence of SEQ ID NO: 6, and the anti-human TLR4 antibody fragment is an scFv consisting of the amino acid sequence of amino acid numbers 491 to 732 of SEQ ID NO: 4.

Preferably, the N terminal of the anti-human TLR4 antibody fragment is connected via linker to the C terminal of each heavy chain of the anti-human TLR2 antibody in the bispecific antibody of the present invention which is an IgG(TLR2)-scFv(TLR4). The structure of such a specific antibody is shown in FIG. 1.

The linker connecting the N terminal of the anti-human TLR4 antibody fragment to the C terminal of each heavy chain of the anti-human TLR2 antibody is a peptide (peptide linker) of any length which connects two terminals. The peptide linker is a peptide preferably having at least 5 amino acids, more preferably at least 10 amino acids, and still more preferably 15 to 50 amino acids. The preferred peptide linker is a GS linker and preferably comprises a plurality of (Gly)$_4$Ser, more preferably five to ten (Gly)$_4$Ser. Such a linker may be, for example, a peptide linker consisting of the amino acid sequence set forth in SEQ ID NO: 9.

In one embodiment, the bispecific antibody of the present invention which is an IgG(TLR2)-scFv(TLR4) is a bispecific antibody wherein the anti-human TLR2 antibody comprises a heavy chain consisting of the amino acid sequence of amino acid numbers 1 to 450 of SEQ ID NO: 4, and a light chain consisting of the amino acid sequence of SEQ ID NO: 6, the anti-human TLR4 antibody fragment is an scFv consisting of the amino acid sequence of amino acid numbers 491 to 732 of SEQ ID NO: 4, and the N terminal of the anti-human TLR4 antibody fragment is connected via linker to the C terminal of each heavy chain of the anti-human TLR2 antibody. The fusion in which the N terminal of the anti-human TLR4 antibody fragment is connected via linker to the C terminal of the heavy chain of the anti-human TLR2 antibody is also referred to as an "anti-human TLR2 antibody heavy chain-anti-human TLR4 antibody scFv fusion". Preferably, in the bispecific antibody, the linker connecting the heavy chain of the anti-human TLR2 antibody and the anti-human TLR4 antibody fragment is a GS linker. More preferably, the GS linker consists of the amino acid sequence of SEQ ID NO: 9. Such a bispecific antibody of the present invention may be, for example, a bispecific antibody comprising an anti-human TLR2 antibody heavy chain-anti-human TLR4 antibody scFv fusion consisting of the amino acid sequence of SEQ ID NO: 4, and a light chain of anti-human TLR2 antibody consisting of the amino acid sequence of SEQ ID NO: 6.

It is generally known that when an antibody is expressed in cells, the antibody is modified after translation. Examples of the post-translational modification include cleavage of lysine at the C terminal of the heavy chain by a carboxypeptidase; and modification of glutamine or glutamic acid at the N terminal of the heavy chain and the light chain to pyroglutamic acid by pyroglutamylation; and it is known that deletion of lysine at the C terminal of the heavy chain and modification of most of glutamine at the N terminal of the heavy chain and the light chain to pyroglutamic acid occur in various antibodies (Journal of Pharmaceutical Sciences, 2008, Vol. 97, p. 2426-2447).

The bispecific antibody binding to human TLR2 and human TLR4 of the present invention also includes a bispecific antibody binding to human TLR2 and human TLR4 and subjected to post-translational modification. For example, the bispecific antibody of the present invention also includes not only a bispecific antibody having a full-length heavy chain, but also a bispecific antibody having a heavy chain lacking lysine at the C terminal. Also included is a bispecific antibody subjected to modification of glutamine or glutamic acid at the N terminal to pyroglutamic acid by pyroglutamylation. It is known in the art that such post-translational modification due to pyroglutamylation at the N terminal and deletion of lysine at the C terminal has no effect on the activity of the antibody (Analytical Biochemistry, 2006, Vol. 348, p. 24-39).

In one embodiment, the bispecific antibody binding to human TLR2 and human TLR4 of the present invention also includes a bispecific antibody described below.

A bispecific antibody binding to human TLR2 and human TLR4, comprising an anti-human TLR2 antibody heavy chain-anti-human TLR4 antibody scFv fusion consisting of the amino acid sequence of SEQ ID NO: 4 and having a modification of glutamic acid of amino acid number 1 of SEQ ID NO: 4 to pyroglutamic acid, and a light chain of an anti-human TLR2 antibody consisting of the amino acid sequence of SEQ ID NO: 6.

The present invention also includes a bispecific antibody that binds to human TLR2 and TLR4 and has the following characteristics.

A bispecific antibody binding to human TLR2 and human TLR4, comprising 1) a heavy chain variable region of an anti-human TLR2 antibody comprising CDR1 consisting of the amino acid sequence of amino acid numbers 31 to 35 of SEQ ID NO: 4, CDR2 consisting of the amino acid sequence of amino acid numbers 50 to 66 of SEQ ID NO: 4, and CDR3 consisting of the amino acid sequence of amino acid numbers 99 to 109 of SEQ ID NO: 4, and a light chain variable region of an anti-human TLR2 antibody comprising CDR1 consisting of the amino acid sequence of amino acid numbers 24 to 39 of SEQ ID NO: 6, CDR2 consisting of the amino acid sequence of amino acid numbers 55 to 61 of SEQ ID NO: 6, and CDR3 consisting of the amino acid sequence of amino acid numbers 94 to 102 of SEQ ID NO: 6; and 2) a heavy chain variable region of an anti-human TLR4 antibody comprising CDR1 consisting of the amino acid sequence of amino acid numbers 521 to 525 of SEQ ID NO:

4, CDR2 consisting of the amino acid sequence of amino acid numbers 540 to 556 of SEQ ID NO: 4, and CDR3 consisting of the amino acid sequence of amino acid numbers 589 to 598 of SEQ ID NO: 4, and a light chain variable region of an anti-human TLR4 antibody comprising CDR1 consisting of the amino acid sequence of amino acid numbers 648 to 658 of SEQ ID NO: 4, CDR2 consisting of the amino acid sequence of amino acid numbers 674 to 680 of SEQ ID NO: 4, and CDR3 consisting of the amino acid sequence of amino acid numbers 713 to 721 of SEQ ID NO: 4.

The method of evaluating an activity of the bispecific antibody of the present invention may include a method of evaluating a binding activity and a neutralizing activity for human TLR2 and/or human TLR4.

Whether or not having a binding activity to human TLR2 or human TLR4 may be confirmed by a known measurement method in the art. Such a measurement method may include, for example, methods such as surface plasmon resonance (SPR) analysis and an Enzyme-Linked ImmunoSorbent Assay (ELISA). For example, in the case of performing an SPR analysis for a binding activity to human TLR2, Biacore T200 (GE Healthcare Japan) may be used. In this case, the binding activity of a test antibody to human TLR2 may be evaluated by immobilizing the human TLR2 protein (R&D Systems) on the surface of a sensor chip, adding the test antibody to a flow path, and analyzing the dissociation constant of the test antibody with the human TLR2 protein (KD). As an example of a specific evaluation method, the method as described in Example 5 below may be used. As another example, in the case of evaluating a binding activity to human TLR4 using ELISA, the binding activity of a test antibody to human TLR4 may be evaluated by immobilizing a human TLR4 and MD2 complex (hereinafter referred to as human TLR4/MD2) protein on an ELISA plate, adding a test antibody thereto, followed by the reaction, allowing to react with a secondary antibody such as anti-IgG antibody labeled with an enzyme such as horseradish peroxidase (HRP), washing, and then activity measurement using an activity detection reagent (for example, in the case of HRP labeling, 3,3′,5,5′-tetramethylbenzidine(TMB; MOS)) to identify the binding of the secondary antibody. As an example of a specific evaluation method, the method as described in Example 9 below may be used.

The term "neutralizing activity of the antibody against human TLR2" refers to an activity that inhibits any biological activity which is elicited by human TLR2 through binding to human TLR2, and one or a plurality of biological activities may be evaluated as an indicator. For example, such a neutralizing activity against human TLR2 may be an activity that inhibits Pam2CSK4-induced AP production in a THP1-xBlue cell which is a human monocytic cell. As a specific method of evaluating the activity, for example, the method as described in Example 6 below may be used.

The term "neutralizing activity of the antibody against human TLR4" refers to an activity that inhibits any biological activity which is elicited by human TLR4 through binding to human TLR4, and one or a plurality of biological activities may be evaluated as an indicator. For example, such a neutralizing activity against human TLR4 may be an activity that inhibits LPS-induced IL-6 production in a U937 cell which is a human monocytic cell line.

The bispecific antibody of the present invention has a neutralizing activity against human TLR2 and human TLR4. The phrase "has a neutralizing activity against human TLR2 and human TLR4" refers to having both a neutralizing activity against human TLR2 and a neutralizing activity against human TLR4. Whether or not having a neutralizing activity against human TLR2 and human TLR4 may be evaluated by using each of the above-mentioned evaluation methods of a neutralizing activity against human TLR2 or human TLR4, and an activity of inhibiting one or a plurality of biological activities of the cell mediated by human TLR2 and human TLR4 may be evaluated by using a cell expressing both of human TLR2 and human TLR4. An example of the latter evaluation method may be an evaluation of an activity that inhibits TNFα production induced by *Pseudomonas aeruginosa* PAO-1 (for example, ATCC: BAA-47) which is the causative agent of sepsis in a human peripheral blood mononuclear cell expressing human TLR2 and human TLR4. The antibody having such an activity may be determined as an antibody having a neutralizing activity against human TLR2 and human TLR4. As a specific evaluation method, the method as described in Example 10 below may be used.

The bispecific antibody binding to human TLR2 and human TLR4 of the present invention may be easily prepared by those skilled in the art using a known method in the art, based on sequence information of the heavy chain variable region and the light chain variable region of an anti-human TLR2 antibody, and the heavy chain variable region and the light chain variable region of an anti-human TLR4 antibody included in the bispecific antibody of the present invention, which are disclosed in the present specification. The bispecific antibody binding to human TLR2 and human TLR4 of the present invention is not particularly limited, but may be produced according to, for example, the method described in the section of <Method for producing bispecific antibody of the present invention, and bispecific antibody produced by the same method> described below.

The bispecific antibody binding to human TLR2 and human TLR4 of the present invention is further purified if desired and formulated according to a conventional method, and then may be used for the prevention or treatment of diseases in which human TLR2 and human TLR4 are involved in the pathogenesis thereof, including immune inflammatory diseases such as sepsis, acute renal failure, chronic kidney disease, acute respiratory distress syndrome, scleroderma, acute pancreatitis, chronic obstructive pulmonary disease.

<Polynucleotide of the Present Invention>

The polynucleotide of the present invention includes a polynucleotide comprising a base sequence encoding the heavy chain variable region (consisting of the amino acid sequence of amino acid numbers 1 to 120 of SEQ ID NO: 4) of an anti-human TLR2 antibody included in the bispecific antibody binding to human TLR2 and human TLR4 of the present invention, a polynucleotide comprising a base sequence encoding the light chain variable region (consisting of the amino acid sequence of amino acid numbers 1 to 113 of SEQ ID NO: 6) of an anti-human TLR2 antibody included in the bispecific antibody binding to human TLR2 and human TLR4 of the present invention, a polynucleotide comprising a base sequence encoding the heavy chain variable region (consisting of the amino acid sequence of amino acid numbers 491 to 609 of SEQ ID NO: 4) of an anti-human TLR4 antibody included in the bispecific antibody binding to human TLR2 and human TLR4 of the present invention, and a polynucleotide comprising a base sequence encoding the light chain variable region (consisting of the amino acid sequence of amino acid numbers 625 to 732 of SEQ ID NO: 4) of an anti-human TLR4 antibody included in the bispecific antibody binding to human TLR2 and human TLR4 of the present invention.

The polynucleotide of the present invention is not particularly limited as long as it is a polynucleotide comprising a base sequence encoding the heavy chain variable region of an anti-human TLR2 antibody included in the bispecific antibody binding to human TLR2 and human TLR4 of the present invention, a polynucleotide comprising a base sequence encoding the light chain variable region of an anti-human TLR2 antibody included in the bispecific antibody, a polynucleotide comprising a base sequence encoding the heavy chain variable region of an anti-human TLR4 antibody included in the bispecific antibody, or a polynucleotide comprising a base sequence encoding the light chain variable region of an anti-human TLR4 antibody included in the bispecific antibody. For example, the polynucleotide comprising a base sequence encoding the heavy chain variable region of the anti-human TLR2 antibody may be a polynucleotide comprising a base sequence of base numbers 1 to 360 of SEQ ID NO: 3, the polynucleotide comprising a base sequence encoding the light chain variable region of the anti-human TLR2 antibody may be a polynucleotide comprising a base sequence of base numbers 1 to 339 of SEQ ID NO: 5, the polynucleotide comprising a base sequence encoding the heavy chain variable region of the anti-human TLR4 antibody may be a polynucleotide comprising a base sequence of base numbers 1471 to 1827 of SEQ ID NO: 3, and the polynucleotide comprising a base sequence encoding the light chain variable region of the anti-human TLR4 antibody may be a polynucleotide comprising a base sequence of base numbers 1873 to 2196 of SEQ ID NO: 3.

Preferred examples of the polynucleotide of the present invention include a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4, and a polynucleotide comprising a base sequence encoding the light chain of an anti-human TLR2 antibody consisting of the amino acid sequence of SEQ ID NO: 6, where the bispecific antibody of the present invention is a polynucleotide comprising a base sequence encoding IgG(TLR2)-scFv(TLR4). The polynucleotide comprising a base sequence encoding an anti-human TLR2 antibody heavy chain-anti-human TLR4 antibody scFv fusion is preferably a polynucleotide comprising a base sequence encoding the fusion of consisting of the amino acid sequence of SEQ ID NO: 4.

In one embodiment, the polynucleotide encoding an anti-human TLR2 antibody heavy chain-anti-human TLR4 antibody scFv fusion consisting of the amino acid sequence of SEQ ID NO: 4 may be a polynucleotide consisting of the base sequence of SEQ ID NO: 3, and the polynucleotide of the light chain of an anti-human TLR2 antibody consisting of the amino acid sequence of SEQ ID NO: 6 may be a polynucleotide consisting of the base sequence of SEQ ID NO: 5.

The polynucleotide of the present invention can be easily prepared by those skilled in the art using a known method in the art based on the base sequence. For example, the polynucleotide of the present invention can be synthesized using a known gene synthesis method in the art. Various methods such as a synthesis method of antibody genes described in WO90/07861 known to those skilled in the art may be used as the gene synthesis method. Once the polynucleotide of the present invention is obtained, it is also possible to obtain other polynucleotides of the present invention by introducing a mutation into a predetermined site of this polynucleotide. The mutagenesis method that may be used includes various methods known to those skilled in the art, such as site-specific mutagenesis (Current Protocols in Molecular Biology edit., 1987, John Wiley&Sons Section 8.1-8.5).

<Expression Vector of the Present Invention>

The expression vector of the present invention includes a vector which is an expression vector comprising a polynucleotide comprising a base sequence encoding the heavy chain variable region of an anti-human TLR2 antibody included in the bispecific antibody binding to human TLR2 and human TLR4 of the present invention, a polynucleotide comprising a base sequence encoding the light chain variable region of an anti-human TLR2 antibody included in the bispecific antibody, a polynucleotide comprising a base sequence encoding the heavy chain variable region of an anti-human TLR4 antibody included in the bispecific antibody, and/or a polynucleotide comprising a base sequence encoding the light chain variable region of an anti-human TLR4 antibody included in the bispecific antibody, and can be used in the production of a bispecific antibody binding to human TLR2 and human TLR4 of the present invention. Bispecific antibodies of various formats and their production methods are known in the art. The expression vector of the present invention can be easily constructed according to these production methods by those skilled in the art in accordance with the format of a bispecific antibody to be expressed.

For example, the expression vector used to produce the bispecific antibody of the present invention which is IgG(TLR2)-scFv(TLR4) is preferably an expression vector comprising one or both of a polynucleotide comprising a base sequence encoding a heavy chain variable region of an anti-human TLR2 antibody included in the bispecific antibody, a heavy chain variable region of an anti-human TLR4 antibody included in the bispecific antibody, and a light chain variable region of an anti-human TLR4 antibody included in the bispecific antibody, and a polynucleotide comprising a base sequence encoding a light chain variable region of an anti-human TLR2 antibody included in the bispecific antibody.

More preferably, the expression vector used to produce the bispecific antibody of the present invention which is IgG(TLR2)-scFv(TLR4) is an expression vector comprising one or both of a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4, and a polynucleotide comprising a base sequence encoding the light chain of an anti-human TLR2 antibody consisting of the amino acid sequence of SEQ ID NO: 6.

Still more preferably, the expression vector used to produce the bispecific antibody of the present invention which is IgG(TLR2)-scFv(TLR4) is an expression vector comprising one or both of a polynucleotide comprising a base sequence encoding an anti-human TLR2 antibody heavy chain-anti-human TLR4 antibody scFv fusion consisting of the amino acid sequence of SEQ ID NO: 4, and a polynucleotide comprising a base sequence encoding the light chain of an anti-human TLR2 antibody consisting of the amino acid sequence of SEQ ID NO: 6.

The expression vector used to express polynucleotides is not particularly limited as long as a polynucleotide comprising a base sequence encoding the heavy chain variable region of an anti-human TLR2 antibody included in the bispecific antibody binding to human TLR2 and human TLR4 of the present invention, a polynucleotide comprising a base sequence encoding the light chain variable region of an anti-human TLR2 antibody included in the bispecific antibody, a polynucleotide comprising a base sequence encoding the heavy chain variable region of an anti-human TLR4 antibody included in the bispecific antibody, and/or a polynucleotide comprising a base sequence encoding the light chain variable region of an anti-human TLR4 antibody included in the bispecific antibody can be expressed in various host cells of eukaryotic cells (for example, animal cells, insect cells, plant cells, and yeast) and/or prokaryotic cells (for example, *Escherichia coli*), and the polypeptides encoded by these polynucleotides can be produced. Examples of the expression vector include a plasmid vector and viral vector (for example, adenovirus or retrovirus). Preferably, pEE6.4 or pEE12.4 (Lonza, Inc.) may be used. Further, an antibody gene may be expressed by introducing a variable region gene fragment into an expression vector comprising a human Ig constant region gene such as AG-γ1 or AG-κ (for example, see WO94/20632) in advance.

In the case where an animal cell, an insect cell, or yeast is used as the host cell, the expression vector of the present invention may comprise a start codon and a stop codon. In this case, the expression vector of the present invention may comprise an enhancer sequence, an untranslated region on the 5' side and the 3' side of genes encoding the bispecific antibody of the present invention or the heavy chain variable region or light chain variable region thereof, a secretory signal sequence, a splicing junction, a polyadenylation site, or a replicon. In the case where *Escherichia coli* is used as the host cell, the expression vector of the present invention may comprise a start codon, a stop codon, a terminator region, and a replicon. In addition, the expression vector of the present invention may comprise a selection marker (for example, a tetracycline resistance gene, an ampicillin resistance gene, a kanamycin resistance gene, a neomycin resistance gene, or a dihydrofolate reductase gene) which is commonly used according to the necessity.

The expression vector of the present invention may include a promoter that is operably linked to the polynucleotide. Examples of the promoter for expressing the polynucleotide of the present invention in an animal cell include a virus-derived promoter such as CMV, RSV, or SV40, an actin promoter, an elongation factor (EF) 1α promoter, and a heat shock promoter. In the case where the host cell is *Escherichia coli* (for example, bacteria belonging to the genus *Escherichia*), examples of the promoters for the expression include a trp promoter, a lac promoter, a XPL promoter, and a tac promoter. Further, examples of promoters for the expression in yeast include a GAL1 promoter, a GAL10 promoter, a PHOS promoter, a PGK promoter, a GAP promoter, and an ADH promoter.

<Transformed Host Cell of the Present Invention>

The transformed host cell of the present invention is not particularly limited as long as it is transformed with the expression vector of the present invention, and an example thereof is the transformed host cell of the present invention used to produce the bispecific antibody of the present invention which is IgG(TLR2)-scFv(TLR4) and includes a host cell transformed with an expression vector comprising one or both of a polynucleotide comprising a base sequence encoding a heavy chain variable region of an anti-human TLR2 antibody included in the bispecific antibody, a heavy chain variable region of an anti-human TLR4 antibody included in the bispecific antibody, and a light chain variable region of an anti-human TLR4 antibody included in the bispecific antibody, and a polynucleotide comprising a base sequence encoding a light chain variable region of an anti-human TLR2 antibody included in the bispecific antibody.

The transformed host cell of the present invention which is IgG(TLR2)-scFv(TLR4) includes a host cell transformed with the expression vector of the present invention, which is selected from the group consisting of the following (a) to (d):

(a) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4, and an expression vector comprising polynucleotide comprising a base sequence encoding a light chain variable region of an anti-human TLR2 antibody consisting of the amino acid sequence of amino acid numbers 1 to 113 of SEQ ID NO: 6;

(b) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, a polynucleotide comprising a base sequence encoding a light chain variable region of an anti-human TLR4 antibody consisting of the amino acid sequence of amino acid numbers 625 to 732 of SEQ ID NO: 4, and a polynucleotide comprising a base sequence encoding a light chain variable region of an anti-human TLR2 antibody consisting of the amino acid sequence of amino acid numbers 1 to 113 of SEQ ID NO: 6;

(c) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4; and (d) a host cell transformed with an expression vector comprising a polynucleotide comprising a base sequence encoding a light chain variable region of an anti-human TLR2 antibody consisting of the amino acid sequence of amino acid numbers 1 to 113 of SEQ ID NO: 6.

In one embodiment, the transformed host cell of the present invention is a host cell transformed with the expression vector of the present invention, which is selected from the group consisting of the following (a) to (d):

(a) a host cell transformed with an expression vector comprising a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4, and an expression vector comprising a polynucleotide comprising a base sequence encoding the light chain of an anti-human TLR2 antibody consisting of the amino acid sequence of SEQ ID NO: 6;

(b) a host cell transformed with an expression vector comprising a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4 and a polynucleotide comprising a base sequence encoding the light chain of an anti-human TLR2 antibody consisting of the amino acid sequence of SEQ ID NO: 6.

(c) a host cell transformed with an expression vector comprising a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4; and (d) a host cell transformed with an expression vector comprising a polynucleotide comprising a base sequence encoding the light chain of an anti-human TLR2 antibody consisting of the amino acid sequence of SEQ ID NO: 6.

In one embodiment, the transformed host cell of the present invention is a host cell transformed with the expression vector of the present invention, which is selected from the group consisting of the following (a) to (d):

(a) a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4, and an expression vector comprising a polynucleotide comprising a base sequence encoding the light chain of an anti-human TLR2 antibody consisting of the amino acid sequence of SEQ ID NO: 6;

(b) a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4 and a polynucleotide comprising a base sequence encoding the light chain of an anti-human TLR2 antibody consisting of the amino acid sequence of SEQ ID NO: 6;

(c) a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4; and (d) a host cell transformed with an expression vector comprising a polynucleotide comprising a base sequence encoding the light chain of an anti-human TLR2 antibody consisting of the amino acid sequence of SEQ ID NO: 6.

Preferred examples of the transformed host cell of the present invention which is IgG(TLR2)-scFv(TLR4) include a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4, and an expression vector comprising a polynucleotide comprising a base sequence encoding the light chain of an anti-human TLR2 antibody consisting of the amino acid sequence of SEQ ID NO: 6, and a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4 and a polynucleotide comprising a base sequence encoding the light chain of an anti-human TLR2 antibody consisting of the amino acid sequence of SEQ ID NO: 6.

The method for producing IgG(TLR2)-scFv(TLR4) of the present invention is not particularly limited as long as it includes a step of culturing the transformed host cell of the present invention to express IgG(TLR2)-scFv(TLR4). Examples of the preferred host cell for use in the method include the foregoing preferred transformed host cells of the present invention.

The host cell to be transformed is not particularly limited as long as the host cell is appropriate for an expression vector being used, is transformed with the expression vector, and can express an antibody. Examples of the host cell to be transformed include various cells such as natural cells or artificially established cells which are conventionally used in the art to which the present invention pertains (for example, animal cells (for example, CHO-K1SV cells), insect cells (for example, Sf9), *Escherichia coli* (for example, bacteria belonging to the genus *Escherichia*), yeast (for example, the genus *Saccharomyces* or *Pichia*), and the like). Preferably, cultured cells of CHO-K1SV cells, CHO-DG44 cells, 293 cells, NS0 cells or the like may be used.

The method of transforming a host cell is not particularly limited, but, for example, a calcium phosphate method or an electroporation method may be used.

<Method for Producing Bispecific Antibody of the Present Invention, and Bispecific Antibody Produced by the Same Method>

The method for producing the bispecific antibody binding to human TLR2 and human TLR4 of the present invention is not particularly limited as long as it includes a step of culturing the transformed host cell of the present invention to express the bispecific antibody binding to human TLR2 and human TLR4. Examples of the preferred host cell for use in the method include the foregoing preferred transformed host cells of the present invention.

In one embodiment, the method for producing the bispecific antibody of the present invention which is IgG(TLR2)-scFv(TLR4) includes a method for producing a bispecific antibody binding to human TLR2 and human TLR4, comprising culturing host cell(s) selected from the group consisting of the following (a) to (c) to express the bispecific antibody binding to human TLR2 and human TLR4:

(a) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4, and an expression vector comprising a polynucleotide comprising a base sequence encoding a light chain variable region of an anti-human TLR2 antibody consisting of the amino acid sequence of amino acid numbers 1 to 113 of SEQ ID NO: 6;

(b) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, a polynucleotide comprising a base sequence encoding a light chain variable region of an anti-human TLR4 antibody consisting of the amino acid sequence of amino acid numbers 625 to 732 of SEQ ID NO: 4, and a polynucleotide comprising a base sequence encoding a light chain variable region of an anti-human TLR2 antibody consisting of the amino acid sequence of amino acid numbers 1 to 113 of SEQ ID NO: 6; and (c) a host cell transformed with an expression vector comprising a polynucleotide comprising a base sequence encoding a heavy chain variable region of an anti-human TLR2 antibody consisting of the amino acid sequence of amino acid numbers 1 to 120 of SEQ ID NO: 4, a polynucleotide comprising a base sequence encoding a heavy chain variable region of an anti-human TLR4 antibody consisting of the amino acid sequence of amino acid numbers 491 to 609 of SEQ ID NO: 4, and a polynucleotide comprising a base sequence encoding a light chain variable region of an anti-human TLR4 antibody consisting of the amino acid sequence of amino acid numbers 625 to 732 of SEQ ID NO: 4, and a host cell transformed with an expression vector comprising a polynucleotide comprising a base sequence encoding a light chain variable region of an anti-human TLR2 antibody consisting of the amino acid sequence of amino acid numbers 1 to 113 of SEQ ID NO: 6.

In one embodiment, the method for producing the bispecific antibody binding to human TLR2 and human TLR4 of the present invention includes a method for producing a bispecific antibody binding to human TLR2 and human TLR4, comprising culturing host cell(s) selected from the group consisting of the following (a) to (c) to express the bispecific antibody binding to human TLR2 and human TLR4:

(a) a host cell transformed with an expression vector comprising a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4, and an expression vector comprising a polynucleotide comprising a base sequence encoding the light chain of an anti-human TLR2 antibody consisting of the amino acid sequence of SEQ ID NO: 6;

(b) a host cell transformed with an expression vector comprising a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4 and a polynucleotide comprising a base sequence encoding the light chain of an anti-human TLR2 antibody consisting of the amino acid sequence of SEQ ID NO: 6; and (c) a host cell transformed with an expression vector comprising a polynucleotide comprising a base sequence encoding an anti-human TLR2 antibody heavy chain-anti-human TLR4 antibody scFv fusion in which the N terminal of an anti-human TLR4 antibody fragment consisting of the amino acid sequence of amino acid numbers 491 to 732 of SEQ ID NO: 4 is connected via a linker to the C terminal of the heavy chain of an anti-human TLR2 antibody consisting of the amino acid sequence of amino acid numbers 1 to 450 of SEQ ID NO: 4, and a host cell transformed with an expression vector comprising a polynucleotide comprising a base sequence encoding the light chain of an anti-human TLR2 antibody consisting of the amino acid sequence of SEQ ID NO: 6.

In one embodiment, the method for producing the bispecific antibody binding to human TLR2 and human TLR4 of the present invention includes a method for producing a bispecific antibody binding to human TLR2 and human TLR4, comprising culturing host cell(s) selected from the group consisting of the following (a) to (c) to express the bispecific antibody binding to human TLR2 and human TLR4:

(a) a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4, and an expression vector comprising a polynucleotide comprising a base sequence encoding the light chain of an anti-human TLR2 antibody consisting of the amino acid sequence of SEQ ID NO: 6;

(b) a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4 and a polynucleotide comprising a base sequence encoding the light chain of an anti-human TLR2 antibody consisting of the amino acid sequence of SEQ ID NO: 6; and (c) a host cell transformed with an expression vector comprising a polynucleotide comprising a base sequence encoding an anti-human TLR2 antibody heavy chain-anti-human TLR4 antibody scFv fusion consisting of the amino acid sequence of SEQ ID NO: 4, and a host cell transformed with an expression vector comprising a polynucleotide comprising a base sequence encoding the light chain of an anti-human TLR2 antibody consisting of the amino acid sequence of SEQ ID NO: 6.

The transformed host cell can be cultured by a known method. The culture conditions, for example, the temperature, pH of the medium, and the culture time are appropriately selected. In the case where the host cell is an animal cell, examples of the medium include an MEM medium containing approximately 5 to 20% fetal bovine serum (Science, 1959, Vol. 130, No. 3373, p. 432 to 7), a DMEM medium (Virology, 1959, Vol. 8, p. 396), and an RPMI1640 medium (J. Am. Med. Assoc., 1967, Vol. 199, p. 519), a 199 medium (Exp. Biol. Med., 1950, Vol. 73, p. 1 to 8). The pH of the medium is preferably about 6 to 8, and the culture is generally carried out at about 30 to 40° C. for about 15 to 72 hours with aeration and stirring if necessary. In the case where the host cell is an insect cell, for example, a Grace's medium (Proc. Natl. Acad. Sci. USA, 1985, Vol. 82, p. 8404) containing fetal bovine serum may be used as the medium. The pH of the medium is preferably about 5 to 8, and the culture is generally carried out at about 20 to 40° C. for about 15 to 100 hours with aeration and stirring if necessary. In the case where the host cell is *Escherichia coli* or yeast, for example, a liquid medium containing a source of nutrients is suitable as the medium. It is preferred that the nutrient medium contains a carbon source, an inorganic nitrogen source or an organic nitrogen source necessary for the growth of the transformed host cell. Examples of the carbon source include glucose, dextran, soluble starch and sucrose, and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the medium is preferably about 5 to 8. In the case where the host cell is *Escherichia coli*, preferred examples of the medium that can be used include an LB medium and an M9 medium (Mol. Clo., Cold Spring Harbor Laboratory, Vol. 3, A2.2). The culture is generally carried out at about 14 to 39° C. for about 3 to 24 hours with aeration and stirring if necessary. In the case where the host cell is yeast, for example, a Burkholder minimal medium (Proc. Natl. Acad, Sci, USA, 1980, Vol. 77, p. 4505) can be used as the medium. The culture is generally carried out at about 20 to 35° C. for about 14 to 144 hours with aeration and stirring if necessary. By carrying out the culture in the above-described manner, it is possible to express the bispecific antibody binding to human TLR2 and human TLR4 of the present invention.

The method for producing the bispecific antibody binding to human TLR2 and human TLR4 of the present invention may further include recovering, preferably isolating or purifying the bispecific antibody of the present invention from the transformed host cell in addition to culturing the transformed host cell to express the bispecific antibody of the present invention as described above. Examples of the isolation or purification method include methods using solubility such as salting-out and a solvent precipitation method, methods using the molecular weight difference such as dialysis, ultrafiltration and gel filtration, methods utilizing an electric charge such as ion exchange chromatography and hydroxylapatite chromatography, methods using specific affinity such as affinity chromatography, methods using the hydrophobicity difference such as reverse phase high performance liquid chromatography, and methods using the isoelectric point difference such as isoelectric point electrophoresis. Preferably, the antibody accumulated in a culture supernatant can be purified by various chromatographies, for example, various column chromatographies using Protein A column or Protein G column.

<Pharmaceutical Composition of the Present Invention>

The pharmaceutical composition of the present invention includes a pharmaceutical composition comprising the bispecific antibody binding to human TLR2 and human TLR4 of the present invention and a pharmaceutically acceptable excipient. The pharmaceutical composition of the present invention may be prepared by a conventionally used method using excipients, that is, pharmaceutical excipients or pharmaceutical carriers commonly used in the art. Examples of dosage forms of the pharmaceutical compositions include parenteral preparations such as an injection and a drip infusion, which can be administered by intravenous administration, subcutaneous administration, or the like. In preparation of pharmaceuticals, carriers and additives in accordance with the dosage forms can be used within the pharmaceutically acceptable range.

The pharmaceutical composition of the present invention may include plural kinds of bispecific antibodies binding to human TLR2 and human TLR4 of the present invention. For example, the present invention also includes a pharmaceutical composition comprising an antibody not subjected to post-translational modification and an antibody or an antigen-binding fragment thereof derived from post-translational modification of the antibody.

In one embodiment, the pharmaceutical composition of the present invention comprising a bispecific antibody binding to human TLR2 and human TLR4 also includes a pharmaceutical composition described below.

A pharmaceutical composition comprising a bispecific antibody binding to human TLR2 and human TLR4 which is a bispecific antibody binding to human TLR2 and human TLR4, comprising 1) a heavy chain variable region of an anti-human TLR2 antibody consisting of the amino acid sequence of amino acid numbers 1 to 120 of SEQ ID NO: 4, and a light chain variable region of an anti-human TLR2 antibody consisting of the amino acid sequence of amino acid numbers 1 to 113 of SEQ ID NO: 6, and 2) a heavy chain variable region of an anti-human TLR4 antibody consisting of the amino acid sequence of amino acid numbers 491 to 609 of SEQ ID NO: 4, and a light chain variable region of an anti-human TLR4 antibody consisting of the amino acid sequence of amino acid numbers 625 to 732 of SEQ ID NO: 4, and a bispecific antibody derived from post-translational modification of the above bispecific antibody.

The pharmaceutical composition of the present invention also includes a pharmaceutical composition comprising a bispecific antibody having the deletion of the C-terminal lysine of the heavy chain, a bispecific antibody having the N terminal post-translational modification, a bispecific antibody having the deletion of the C-terminal lysine of the heavy chain and N terminal post-translational modification, and/or a bispecific antibody having lysine of the C terminal of the heavy chain and having no N terminal post-translational modification.

In one embodiment, the present invention also includes a pharmaceutical composition comprising a bispecific antibody binding to human TLR2 and human TLR4 of the following (1) and (2).

(1) a bispecific antibody binding to human TLR2 and human TLR4, comprising an anti-human TLR2 antibody heavy chain-anti-human TLR4 antibody scFv fusion consisting of the amino acid sequence of SEQ ID NO: 4 and having a modification of glutamic acid of amino acid number 1 to pyroglutamic acid, and a light chain of an anti-human TLR2 antibody consisting of the amino acid sequence of SEQ ID NO: 6.

(2) a bispecific antibody binding to human TLR2 and human TLR4, comprising an anti-human TLR2 antibody heavy chain-anti-human TLR4 antibody scFv fusion consisting of the amino acid sequence of SEQ ID NO: 4, and a light chain of an anti-human TLR2 antibody consisting of the amino acid sequence of SEQ ID NO: 6.

In yet another embodiment, the pharmaceutical composition of the present invention comprising a bispecific antibody binding to human TLR2 and human TLR4 also includes a pharmaceutical composition described below.

A pharmaceutical composition comprising a bispecific antibody binding to human TLR2 and human TLR4, comprising an anti-human TLR2 antibody heavy chain-anti-human TLR4 antibody scFv fusion consisting of the amino acid sequence set forth in SEQ ID NO: 4 and a light chain of an anti-human TLR2 antibody consisting of the amino acid sequence set forth in SEQ ID NO: 6, and a pharmaceutically acceptable excipient.

The addition amount of the bispecific antibody binding to human TLR2 and human TLR4 of the present invention in a formulation varies depending on severity and age of patients, a dosage form of the drug formulation to be used, the binding titer of the antibody, and the like. For example, the bispecific antibody may be used in an amount of about 0.001 mg/kg to 100 mg/kg.

The pharmaceutical composition of the present invention can be used as an agent for preventing or treating immune inflammatory diseases in which human TLR2 and TLR4 are involved in the pathogenesis thereof, such as sepsis, acute renal failure, chronic renal disease, acute respiratory distress syndrome, scleroderma, acute pancreatitis, and chronic obstructive pulmonary disease.

The present invention includes a pharmaceutical composition for preventing or treating an immune inflammatory disease, comprising the bispecific antibody binding to human TLR2 and human TLR4 of the present invention. Further, the present invention includes a method for preventing or treating an immune inflammatory disease, comprising administering a therapeutically effective amount of the bispecific antibody. Further, the present invention includes the bispecific antibody of the present invention for use in preventing or treating an immune inflammatory disease. In addition, the present invention includes use of the bispecific antibody of the present invention in the manufacture of a pharmaceutical composition for preventing or treating an immune inflammatory disease.

<Anti-Human TLR2 Antibody of the Present Invention and Pharmaceutical Composition Comprising the Same Antibody>

The present invention includes an anti-human TLR2 antibody or an antigen-binding fragment thereof, comprising a heavy chain variable region of an anti-human TLR2 antibody comprising CDR1 consisting of the amino acid sequence of amino acid numbers 31 to 35 of SEQ ID NO: 8, CDR2 consisting of the amino acid sequence of amino acid numbers 50 to 66 of SEQ ID NO: 8, and CDR3 consisting of the amino acid sequence of amino acid numbers 99 to 109 of SEQ ID NO: 8, and a light chain variable region of an anti-human TLR2 antibody comprising CDR1 consisting of the amino acid sequence of amino acid numbers 24 to 39 of SEQ ID NO: 6, CDR2 consisting of the amino acid sequence of amino acid numbers 55 to 61 of SEQ ID NO: 6, and CDR3 consisting of the amino acid sequence of amino acid numbers 94 to 102 of SEQ ID NO: 6.

Further, the present invention also includes an anti-human TLR2 antibody or an antigen-binding fragment thereof comprising a heavy chain variable region consisting of the amino acid sequence of amino acid numbers 1 to 120 of SEQ ID NO: 8 and a light chain variable region consisting of the amino acid sequence of amino acid numbers 1 to 113 of SEQ ID NO: 6, and an antibody or an antigen-binding fragment thereof derived from post-translational modification of the antibody or the antigen-binding fragment thereof. Examples of the post-translational modification include pyroglutamylation at the N terminal of the heavy chain variable region and/or deletion of lysine at the C terminal of the heavy chain. Preferred heavy chain constant region and light chain constant region in the anti-human TLR2 antibody or the antigen-binding fragment thereof of the present invention are the same as those described for the anti-human TLR2 antibody in the section <Bispecific antibody of the present invention> described above.

In one embodiment, the anti-human TLR2 antibody of the present invention is an anti-human TLR2 antibody having the following characteristics.

An anti-human TLR2 antibody comprising a heavy chain consisting of the amino acid sequence of amino acid numbers 1 to 450 of SEQ ID NO: 8 and a light chain consisting of the amino acid sequence of SEQ ID NO: 6.

In yet another embodiment, the anti-human TLR2 antibody of the present invention is an anti-human TLR2 antibody having the following characteristics.

An anti-human TLR2 antibody comprising a heavy chain consisting of the amino acid sequence of amino acid numbers 1 to 449 of SEQ ID NO: 8 and a light chain consisting of the amino acid sequence of SEQ ID NO: 6.

The anti-human TLR2 antibody or the antigen-binding fragment thereof of the present invention can be easily prepared by those skilled in the art using a polynucleotide comprising a base sequence encoding each of the heavy chain variable region and the light chain variable region of the anti-human TLR2 antibody included in the bispecific antibody of the present invention described above, and with reference to the description of <Expression vector of the present invention>, <Transformed host cell of the present invention> and <Method for producing bispecific antibody of the present invention and bispecific antibody produced by the same method> described above.

The present invention also includes a pharmaceutical composition comprising the anti-human TLR2 antibody or the antigen-binding fragment thereof of the present invention and a pharmaceutically acceptable excipient. The pharmaceutical composition of the present invention can be prepared by a conventionally used method using excipients, that is, pharmaceutical excipients or pharmaceutical carriers commonly used in the art. Examples of dosage forms of the pharmaceutical compositions include parenteral preparations such as an injection and a drip infusion, which can be administered by intravenous administration, subcutaneous administration, or the like. In preparation of pharmaceuticals, excipients, carriers, and additives in accordance with the dosage forms can be used within the pharmaceutically acceptable range.

The pharmaceutical composition of the present invention may include plural kinds of anti-human TLR2 antibodies or the antigen-binding fragments thereof of the present invention. For example, the present invention also includes a pharmaceutical composition comprising an antibody or an antigen-binding fragment thereof not subjected to post-translational modification and an antibody or an antigen-binding fragment thereof derived from post-translational modification of the antibody or the antigen-binding fragment thereof.

In one embodiment, the pharmaceutical composition of the present invention comprising an anti-human TLR2 antibody or an antigen-binding fragment thereof also includes a pharmaceutical composition described below.

A pharmaceutical composition comprising an anti-human TLR2 antibody or an antigen-binding fragment thereof comprising a heavy chain variable region consisting of the amino acid sequence of amino acid numbers 1 to 120 of SEQ ID NO: 8 and a light chain variable region consisting of the amino acid sequence of amino acid numbers 1 to 113 of SEQ ID NO: 6, and an anti-human TLR2 antibody or an antigen-binding fragment thereof which is an antibody or an antigen-binding fragment thereof derived from post-translational modification of the antibody or the antigen-binding fragment thereof.

In one embodiment, the pharmaceutical composition of the present invention comprising an anti-human TLR2 antibody also includes a pharmaceutical composition comprising an antibody binding to human TLR2 of the following (1) to (4).

(1) an anti-human TLR2 antibody comprising a heavy chain consisting of the amino acid sequence of amino acid numbers 1 to 449 of SEQ ID NO: 8 and a light chain consisting of the amino acid sequence set forth in SEQ ID NO: 6.

(2) an anti-human TLR2 antibody comprising a heavy chain consisting of the amino acid sequence set forth in SEQ ID NO: 8 and having a modification of glutamic acid of amino acid number 1 to pyroglutamic acid, and a light chain consisting of the amino acid sequence set forth in SEQ ID NO: 6.

(3) an anti-human TLR2 antibody comprising a heavy chain consisting of the amino acid sequence of amino acid numbers 1 to 449 of SEQ ID NO: 8 and having a modification of glutamic acid of amino acid number 1 to pyroglutamic acid, and a light chain consisting of the amino acid sequence set forth in SEQ ID NO: 6.

(4) an anti-human TLR2 antibody comprising a heavy chain consisting of the amino acid sequence set forth in SEQ ID NO: 8 and a light chain consisting of the amino acid sequence set forth in SEQ ID NO: 6.

In yet another embodiment, the pharmaceutical composition of the present invention comprising an anti-human TLR2 antibody also includes the following pharmaceutical composition comprising an antibody binding to human TLR2.

A pharmaceutical composition comprising an anti-human TLR2 antibody comprising a heavy chain consisting of the amino acid sequence of amino acid numbers 1 to 450 of SEQ ID NO: 8 and a light chain consisting of the amino acid sequence of SEQ ID NO: 6, an anti-human TLR2 antibody comprising a heavy chain consisting of the amino acid sequence of amino acid numbers 1 to 449 of SEQ ID NO: 8 and a light chain consisting of the amino acid sequence of SEQ ID NO: 6, and a pharmaceutically acceptable excipient.

The addition amount of the anti-human TLR2 antibody or the antigen-binding fragment thereof of the present invention in a formulation varies depending on severity and age of patients, a dosage form of the drug formulation to be used, the binding titer of the antibody, and the like. For example, the anti-human TLR2 antibody or the antigen-binding fragment thereof may be used in an amount of about 0.001 mg/kg to 100 mg/kg.

The anti-human TLR2 antibody or the antigen-binding fragment thereof of the present invention is further purified if necessary and is formulated according to a conventional method, and then can be used in the treatment of a disease in which human TLR2 is involved in the pathogenesis thereof, such as sepsis or cancer.

<Fusion Antibody and Modified Antibody>

Those skilled in the art can prepare a fusion antibody of a bispecific antibody binding to human TLR2 and human TLR4, an anti-human TLR2 antibody or an antigen-binding fragment thereof with another peptide or protein and can also prepare a modified antibody having a modifying agent bound thereto, using a known method in the art. The bispecific antibody binding to human TLR2 and human TLR4, the anti-human TLR2 antibody or the antigen-binding fragment thereof of the present invention also includes an antibody and an antigen-binding fragment thereof in the form of such a fusion or a modification. The other peptide or protein that can be used for the fusion is not particularly limited, as long as the bispecific antibody binding to human TLR2 and human TLR4 of the present invention as the fusion antibody has a binding activity to human TLR2 and human TLR4 or the anti-human TLR2 antibody or the antigen-binding fragment thereof of the present invention as the fusion antibody has a binding activity to human TLR2; examples thereof include human serum albumin, various tag peptides, artificial helix motif peptide, maltose-binding proteins, glutathione S transferase, various toxins, other peptides or proteins capable of promoting multimerization, and the like. The modifying agent that can be used for the modification is not particularly limited, as long as the bispecific antibody binding to human TLR2 and human TLR4 of the present invention as the fusion antibody has a binding activity to human TLR2 and human TLR4 or the anti-human TLR2 antibody or the antigen-binding fragment thereof of the present invention as the modified antibody has a binding activity to human TLR2; examples thereof include polyethylene glycol, sugar chains, phospholipids, liposomes, low-molecular compounds and the like.

The present invention has been described and specific examples referred to for better understanding will be provided, but these are merely examples and the present invention is not limited thereto.

EXAMPLES

With regard to parts using commercially available kits or reagents, the experiments were carried out according to the attached protocol unless otherwise noted. For the sake of convenience, the concentration mol/L is expressed as M. For example, a 1M sodium hydroxide aqueous solution refers to a 1 mol/L aqueous solution of sodium hydroxide.

Example 1: Preparation of Anti-Human TLR2 Antibody-Producing Hybridoma

An anti-human TLR2 antibody was prepared using human monoclonal antibody development technology "VelocImmune" (VelocImmune antibody technology: Regeneron, Inc. (U.S. Pat. No. 6,596,541)) mice. A human TLR2 protein (R&D Systems, 2616-TR-050) was immunized into VelocImmune mice, together with an adjuvant that elicits an immune reaction. According to a conventional method, the spleen or lymph node of the immunized mice was extracted, and lymphocytes were collected and cell-fused with mouse myeloma cells SP2/0 (ATCC: CRL-1581) to prepare a hybridoma. The hybridoma was subjected to monoclonization and cultured in a CD hybridoma medium (Life Technologies) which is a serum-free medium. The antibody was purified from the resulting culture supernatant using a protein G column (GE Healthcare Japan). Since the VelocImmune technology employs transgenic mice in which the endogenous immunoglobulin heavy and light chain variable regions are replaced with the corresponding human variable regions, the antibody obtained is an antibody having variable regions of the human antibody and constant regions of the mouse antibody (also referred to as a chimeric antibody).

Example 2: Evaluation of Neutralizing Activity of Anti-Human TLR2 Antibody

In order to evaluate a neutralizing activity of the anti-human TLR2 antibody identified in Example 1, an assay for the inhibition of a TLR2/6 agonist Pam2CSK4-induced alkaline phosphatase (AP) production was carried out using a THP1-xBlue cell which is a human monocytic cell endogenously expressing human TLR2.

As a result, it was demonstrated that the anti-human TLR2 antibody (chimeric antibody) designated 31-5F5-2F3 inhibits the production of AP and has a neutralizing activity against human TLR2.

Example 3: Sequencing of Anti-Human TLR2 Antibody and Preparation of Variant

The sequence of the genes encoding the heavy chain and light chain of the antibody was analyzed and sequenced from a hybridoma producing the anti-human TLR2 antibody 31-5F5-2F3.

In order to improve physical properties and stability of the antibody following antibody sequencing, FRs of the heavy chain and light chain of 31-5F5-2F3 were replaced with FRs of a different human antibody to prepare an anti-human TLR2 antibody 31-5F5-2F3.m1

Example 4: Preparation of Fully Human Anti-Human TLR2 Antibody

The antibody prepared in Example 3 is an antibody in which the variable region is human-derived and the constant region is mouse-derived. Accordingly, using a GS vector (Lonza, Inc.) which is a mammalian cell expression vector, an expression vector comprising both genes of the heavy chain and the light chain was constructed to thereby produce a fully human antibody. Specifically, a gene encoding a signal sequence (Nigel Whittle et al., Protein Engineering, 1987, Vol. 1, No. 6, p. 499-505) was connected to the 5' side of the heavy chain variable region gene of the 31-5F5-2F3.m1 antibody and a constant region gene of human Igγ1 (consisting of the base sequence of base numbers 361 to 1350 of SEQ ID NO: 7) was connected to the 3' side thereof, and then this heavy chain gene was inserted into a GS vector pEE6.4. Further, a gene encoding a signal sequence (Nigel Whittle, et al., supra) was connected to the 5' side of the light chain variable region gene and a constant region gene of the human κ chain (consisting of the base sequence of amino acid numbers 340 to 657 of SEQ ID NO: 5) was connected to the 3' side thereof, and then this light chain gene was inserted into a GS vector pEE12.4.

The heavy chain gene sequence of an antibody inserted into pEE6.4, and the light chain gene sequence of an antibody inserted into pEE12.4 were analyzed using a sequencer, and from the resulting amino acid sequence, the CDR sequences were determined with reference to the database of Kabat et al ("Sequences of Proteins of Immunological Interest", US Department of Health and Human Services, US Government Printing Office).

The base sequence of the heavy chain of the fully human antibody (fully human 31-5F5-2F3.m1) of the prepared 31-5F5-2F3.m1 is set forth in SEQ ID NO: 7, the amino acid sequence encoded by the base sequence is set forth in SEQ ID NO: 8, the base sequence of the light chain of the antibody is set forth in SEQ ID NO: 5, and the amino acid sequence encoded by the base sequence is set forth in SEQ ID NO: 6.

The heavy chain variable region set forth in SEQ ID NO: 8 consists of the amino acid sequence of amino acid numbers 1 to 120 of SEQ ID NO: 8, and the CDR1, CDR2, and CDR3 of the heavy chain each consist of the amino acid sequence of amino acid numbers 31 to 35, 50 to 66, and 99 to 109 of SEQ ID NO: 8. The variable region of the light chain set forth in SEQ ID NO: 6 consists of the amino acid sequence of amino acid numbers 1 to 113 of SEQ ID NO: 6, and the CDR1, CDR2, and CDR3 of the light chain each consist of the amino acid sequence of amino acid numbers 24 to 39, 55 to 61, and 94 to 102 of SEQ ID NO: 6.

Using the above-described GS vectors into which the genes of the heavy chain and the light chain of the antibody were respectively inserted, the antibody expression was carried out in two ways of transient expression and constitutive expression. For transient expression, both of the above-described expression vectors of the heavy chain and the light chain were transfected into FreeStyle 293 cells (Life Technologies) cultured at about $1 \times 10^6$ cells/mL in a FreeStyle 293 Expression medium (Life Technologies) using a transfection reagent 293fectin (Life Technologies), and cultured for 7 days. Alternatively, both of the above-described expression vectors of the heavy chain and the light chain were transfected into Expi293 cells (Life Technologies) cultured at about $3 \times 10^6$ cells/mL in an Expi293 Expression medium (Life Technologies) using a transfection reagent ExpiFectamine293 (Life Technologies), and cultured for 7 days. Alternatively, both of the above-described expression vectors of the heavy chain and the light chain were transfected into CHO-K1SV cells (Lonza, Inc.) cultured at about $1 \times 10^7$ cells/mL in a CD-CHO medium (Life Technologies) using an electroporation method, and cultured for 7 days. The culture supernatant was purified using a protein A or protein G columns (both are available from GE Healthcare Japan) to give a purified antibody of the fully human antibody. For constitutive expression, the above-described GS vectors into which the genes of the heavy chain and the light chain of the antibody had been respectively inserted were cleaved with the restriction enzymes NotI and PvuI and ligated to each other using Ligation-Convenience Kit (NIPPONGENE) which is a ligation kit or Ligation-high (TOYOBO) which is a ligation reagent, thereby constructing GS vectors in which both genes of the heavy chain and the light chain were inserted. The expression vectors encode a full-length heavy chain and light chain and a glutamine synthetase, and the antibodies were expressed by transfection thereof into CHO-K1SV cells. The culture supernatant was purified using a protein A column or protein G column to obtain a purified antibody of the fully human antibody.

Example 5: Evaluation of Binding Activity of Fully Human Anti-Human TLR2 Antibody To evaluate a binding activity of the fully human 31-5F5-2F3.m1 prepared in Example 4 for human TLR2, an SPR analysis was carried out.

In the SPR analysis, Biacore T200 (GE Healthcare Japan) was used to carry out analysis. An Anti-His IgG (enclosed in His Capture Kit) was immobilized on a sensor chip CM5 (GE Healthcare Japan, BR-1005-30) using a His Capture Kit (GE Healthcare Japan, 28-9950-56) and Amine Coupling Kit (GE Healthcare Japan, BR-1000-50). Flow path No. 1 is referred to as a reference, onto which the human TLR2 protein was not attached. Onto each of other flow paths (No. 2, No. 3, and No. 4), a human TLR2 protein (R&D Systems, 2616-TR-050) diluted to 0.66 µg/mL in HBS-EP+ buffer (GE Healthcare Japan, BR-1006-69) was added at a flow rate of 5 µL/minute for 2 minutes and then immobilized. Thereafter, a solution of fully human 31-5F5-2F3.m1 diluted to 200 nM in HBS-EP+ buffer was added at a flow rate of 50 µL/minute for 2 minutes, and the fully human antibody-human TLR2 binding was measured. Next, HBS-EP+ buffer was added at a flow rate of 50 µL/minute for 5 minutes and the dissociation of the fully human antibody and human TLR2 was measured. Bivalent analyte model and the Rmax were analyzed by Fit local to calculate the association rate constant (ka) and dissociation rate constant (kd), and the association-dissociation constant (KD) was calculated by dividing kd by ka.

As a result, it was demonstrated that KD is 88.5 pM, and the fully human 31-5F5-2F3.m1 has a binding activity to human TLR2.

Example 6: Evaluation of Neutralizing Activity of Fully Human Anti-Human TLR2 Antibody In order to evaluate a neutralizing activity of the fully human 31-5F5-2F3.m1 prepared in Example 4 against human TLR2, an assay for the inhibition of Pam2CSK4-induced AP production was performed using THP1-xBlue cells. THP1-xBlue cells (Invivogen Inc., thpx-sp) were seeded under an RPMI1640 medium (Life Technologies) to $5 \times 10^4$ cells/well in a 96-well plate (Becton, Dickinson and Company) at 75 µL/well. Immediately after cell seeding, 25 µL of fully human 31-5F5-2F3.m1 diluted in 9 steps in a range from 855 nM to 2.19 pM with an RPMI1640 medium was added and incubated for 30 minutes under the conditions of 37° C. and 5% $CO_2$. In addition, 25 µL of Pam2CSK4 (Invivogen, tlrl-pm2s; a final concentration of 100 ng/mL) diluted with an RPMI1640 medium was added. As a control, a well to which an RPMI1640 medium had been added instead of an antibody, and a well to which an RPMI1640 medium had been added instead of Pam2CSK4 were respectively prepared. After culturing overnight under the conditions of 37° C. and 5% $CO_2$, the culture supernatant was collected and the AP concentration in the culture supernatant was measured using a commercially available Quanti-Blue (Invivogen). In addition, an IC50 value of the antibody against Pam2CSK4-induced AP production was calculated. In connection with the calculation of an IC50 value, the well to which an RPMI1640 medium had been added instead of an antibody was set as a 0% inhibition control, and the well to which an RPMI1640 medium had been added instead of Pam2CSK4 was set as a 100% inhibition control. The IC50 value was calculated by four-parameter logistic curve fitting.

As a result, the fully human 31-5F5-2F3.m1 inhibited the AP production and had an IC50 value of 97.7 pM. The fully human 31-5F5-2F3.m1 was found to have a neutralizing activity against human TLR2.

(Example 7: Evaluation of Neutralizing Activity of Fully Human Anti-Human TLR2 Antibody (2))

In order to evaluate a neutralizing activity of the fully human 31-5F5-2F3.m1 prepared in Example 4 against human TLR2, an assay for the inhibition of a Pam2CSK4-induced AP production was carried out using THP1-xBlue cells. T2.5 (Patent Document 1) and OPN305 (Patent Document 3), which are an anti-human TLR2 antibody, were used as comparative antibodies.

The same experiment as in Example 6 was carried out for three types of antibodies, fully human 31-5F5-2F3.m1 (9-step dilution in a range from 855 nM to 2.19 pM in an RPMI1640 medium), T2.5 (9-step dilution in a range from 833 nM to 2.13 pM in an RPMI1640 medium), and OPN305 (9-step dilution in a range from 861 nM to 2.20 pM in an RPMI1640 medium). IC50 values were calculated by four-parameter logistic curve fitting.

Figure 2:
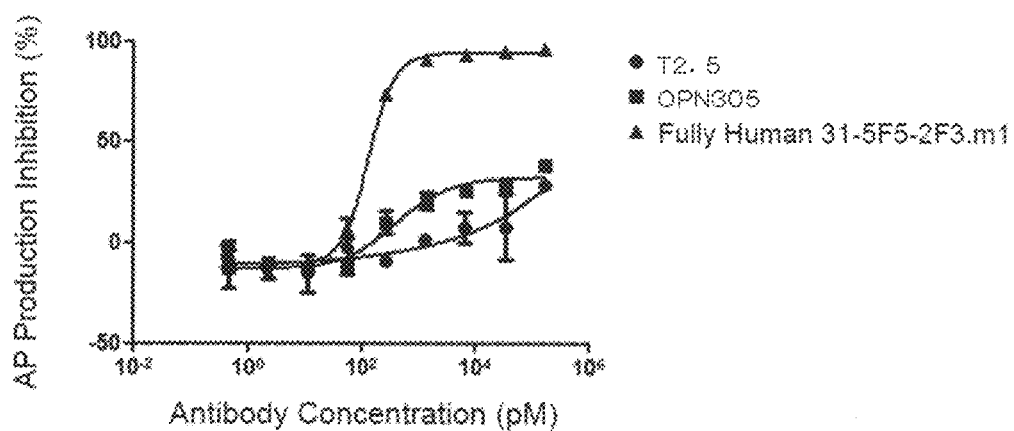
FIG. 2 shows an inhibitory effect of each anti-human TLR2 antibody on Pam2CSK4 (TLR2/6 agonist)-induced alkaline phosphatase (AP) production for THP1-xBlue cells.

As a result, the fully human 31-5F5-2F3.m1 completely inhibited the Pam2CSK4-induced AP production and had an IC50 value of 130 pM. On the other hand, Pam2CSK4-induced AP production inhibition of T2.5 and OPN305 was partial (FIG. 2).

Example 8: Preparation of Bispecific Antibody Binding to Human TLR2 and Human TLR4

Two anti-human TLR2 and anti-human TLR4 bispecific antibodies comprising an anti-human TLR2 antibody (IgG antibody) and an anti-human TLR4 antibody single chain variable region fragment (scFv) were prepared. The bispecific antibodies prepared in this Example is a bispecific antibody of the above-mentioned IgG(TLR2)-scFv(TLR4) type, and has a structure in which the N terminal of the anti-human TLR4 antibody scFv is connected via a linker to the C terminal of each heavy chain of the anti-human TLR2 antibody (FIG. 1).

The gene encoding an anti-human TLR2 antibody heavy chain-anti-human TLR4 antibody scFv fusion was prepared in which the gene encoding a GS linker (SEQ ID NO: 9) was connected to the 3' terminal of the heavy chain gene of the fully human 31-5F5-2F3.m1 prepared in Example 4 using a PCR method, the gene encoding an anti-human TLR4 antibody scFv was connected to the 3' terminal of the gene encoding a GS linker using a PCR method, and the C terminal of the heavy chain of fully human 31-5F5-2F3.m1 and the N terminal of an anti-human TLR4 antibody scFv were connected by the GS linker. The anti-human TLR4 antibody scFv included in the fusion encoded by this gene has a structure in which the N terminal of the light chain variable region consisting of the amino acid sequence of amino acid numbers 625 to 732 of SEQ ID NO: 4 was connected via a GS linker (SEQ ID NO: 10) to the C terminal of the heavy chain variable region consisting of the amino acid sequence of amino acid numbers 491 to 732 of SEQ ID NO: 4 and consisting of the amino acid sequence of amino acid numbers 491 to 609 of SEQ ID NO: 4. The thus-prepared anti-human TLR2 antibody heavy chain-anti-human TLR4 antibody scFv fusion is referred to as an ICU-1-Igγ1 heavy chain. The gene encoding a signal sequence (Nigel Whittle et al., supra) was connected to the 5' side of the ICU-1-Igγ1 heavy chain gene, which was then inserted into a pEE6.4 vector.

In addition, the gene of a modified ICU-1-Igγ1 heavy chain with introduction of amino acid mutations of L234A, L235A, and I253A into the human Igγ1 heavy chain constant region of the ICU-1-Igγ1 heavy chain (referred to as ICU-1-Igγ1-LAsh heavy chain) was prepared and the gene was inserted into a pEE6.4 vector.

Two kinds of bispecific antibodies binding to human TLR2 and human TLR4 were prepared by combining the pEE6.4 vector with insertion of the ICU-1-Igγ1 heavy chain gene or ICU-1-Igγ1-LAsh heavy chain gene and pEE12.4 with insertion of the light chain gene of the fully human 31-5F5-2F3.m1 prepared in Example 4, and using the same method as the expression and purification method of antibodies described in Example 4.

The bispecific antibody comprising the ICU-1-Igγ1 heavy chain and the light chain of fully human 31-5F5-2F3.m1 is referred to as fully human ICU-1-Igγ1, and the bispecific antibody comprising the ICU-1-Igγ1-LAsh heavy chain and the light chain of fully human 31-5F5-2F3.m1 is referred to as fully human ICU-1-Igγ1-LAsh.

The base sequence of the ICU-1-Igγ1 heavy chain of fully human ICU-1-Igγ1 is set forth in SEQ ID NO: 1, and the amino acid sequence encoded by the base sequence is set forth in SEQ ID NO: 2. The base sequence of the ICU-1-Igγ1-LAsh heavy chain of fully human ICU-1-Igγ1-LAsh is set forth in SEQ ID NO: 3, and the amino acid sequence encoded by the base sequence is set forth in SEQ ID NO: 4.

The anti-human TLR2 antibody heavy chain included in the anti-human TLR2 antibody heavy chain-anti-human TLR4 antibody scFv fusion set forth in SEQ ID NO: 2 consists of the amino acid sequence of amino acid numbers 1 to 450 of SEQ ID NO: 2.

The anti-human TLR2 antibody heavy chain included in the anti-human TLR2 antibody heavy chain-anti-human TLR4 antibody scFv fusion set forth in SEQ ID NO: 4 consists of the amino acid sequence of amino acid numbers 1 to 450 of SEQ ID NO: 4.

The variable region of the anti-human TLR2 antibody heavy chain included in the above two anti-human TLR2 antibody heavy chain-anti-human TLR4 antibody scFv fusions set forth in SEQ ID NO: 2 and SEQ ID NO: 4 is common therebetween and consists of the amino acid sequence of amino acid numbers 1 to 120 of SEQ ID NO: 4, and CDR1, CDR2 and CDR3 of the heavy chain variable region each consist of the amino acid sequence of amino acid numbers 31 to 35, 50 to 66, and 99 to 109 of SEQ ID NO: 4.

The anti-human TLR4 antibody scFv included in the above two anti-human TLR2 antibody heavy chain-anti-human TLR4 antibody scFv fusions set forth in SEQ ID NO: 2 and SEQ ID NO: 4 is common therebetween and consists of the amino acid sequence of amino acid numbers 491 to 732 of SEQ ID NO: 4, and the heavy chain variable region of the anti-human TLR4 antibody constituting the anti-human TLR4 antibody scFv consists of the amino acid sequence of amino acid numbers 491 to 609 of SEQ ID NO: 4, and CDR1, CDR2 and CDR3 of the heavy chain variable region each consist of the amino acid sequence of amino acid numbers 521 to 525, 540 to 556, and 589 to 598 of SEQ ID NO: 4. The light chain variable region of the anti-human TLR4 antibody constituting the anti-human TLR4 antibody scFv consists of the amino acid sequence of amino acid numbers 625 to 732 of SEQ ID NO: 4, and CDR1, CDR2 and CDR3 of the light chain variable region each consist of the amino acid sequence of amino acid numbers 648 to 658, 674 to 680, and 713 to 721 of SEQ ID NO: 4.

The base sequence of the light chain of fully human ICU-1-Igγ1 and fully human ICU-1-Igγ1-LAsh is common therebetween and, the base sequence is set forth in SEQ ID NO: 5, and the amino acid sequence encoded by the base sequence is set forth in SEQ ID NO: 6. The variable region of the anti-human TLR2 antibody light chain set forth in SEQ ID NO: 6 consists of the amino acid sequence of amino acid numbers 1 to 113 of SEQ ID NO: 6, and CDR1, CDR2 and CDR3 of the light chain variable region each consist of the amino acid sequence of amino acid numbers 24 to 39, 55 to 61, and 94 to 102 of SEQ ID NO: 6.

Example 9: Evaluation of Binding Activity of Bispecific Antibody Binding to Human TLR2 and Human TLR4

In order to evaluate the binding activity of each of two bispecific antibodies prepared in Example 8 for human TLR2 and human TLR4, ELISA was carried out using a human TLR2 protein and a human TLR4/MD2 protein. 15 µL/well of a human TLR2 protein (R&D Systems, 2616-TR-050) diluted to a concentration of 10 µg/mL in PBS (Life Technologies, 10010-023) was added to a MaxiSorp 384-well plate Clear (Thermo Fisher Scientific Inc.), followed by immobilization at room temperature for 1 hour. Similarly, 15 µL/well of a human TLR4/MD2 protein (R&D Systems, 3146-TM/CF) was added at 10 µg/mL, followed by immobilization at room temperature for 1 hour. After 1 hour, the wells were washed three times with a washing solution (0.05% Tween-20-containing Tris-buffered saline (TBS)), and 100 µL/well of Blocking One (NACALAI TESQUE, INC., 03953-95) was added, followed by blocking at room temperature for 1 hour. The wells were washed again three times with a washing solution, 15 µL/well of two bispecific antibodies prepared in Example 8 was added to the well on which the human TLR2 protein was immobilized and the well on which the human TLR4/MD2 protein was immobilized. The dilution of these antibodies was carried out using reaction buffer where PBS and Blocking One were mixed in equal amounts. The antibodies were diluted in 13 steps in a range from 75.0 nM to 4.47 fM. After allowing to stand at room temperature for 1 hour, the wells were washed three times with a washing solution. 15 µL/well of Human IgG-heavy and light chain cross-adsorbed Antibody (BETHYL, A80-219P) diluted 4000-fold in reaction buffer was added, followed by allowing to stand at room temperature for 1 hour. The wells were washed three times with a washing solution, and 15 µL/well of TMB PEROXIDASE SUBSTRATE ELISA (MOSS, #TMBE-500) was added. After 15 minutes, the reaction was stopped by adding 15 µL/well of 1M sulfuric acid (Wako Pure Chemical Industries, Ltd., 198-09595) to the wells on which the human TLR2 protein was immobilized. After 5 minutes, the reaction was stopped by adding 15 µL/well of 1M sulfuric acid to the wells on which the human TLR4/MD2 protein was immobilized. An absorbance at 450 nm was measured by using Safire2 (TECAN), and an EC50 value of each antibody for the human TLR2 protein and the human TLR4/MD2 protein was calculated. In connection with the calculation of an EC50 value, from the shape of the sigmoidal curve on the graph depicting the measurement value on a vertical axis and the antibody concentration value on a horizontal axis, the maximum value of the measurement values of each antibody that can be determined that the measurement value according to an increase in antibody concentration has reached a convergence value was set to 100%, and the minimum value of the measurement values of each antibody that can be determined that the measurement value according to an decrease in antibody concentration has reached a convergence value was set to 0%. EC50 values calculated by four-parameter logistic curve fitting are shown below (Tables 1 and 2).

TABLE 1

Binding activity to human TLR2 protein

|  | EC50 value (pM) |
|---|---|
| Fully human ICU-1-Igγ1-LAsh | 210.5 |
| Fully human ICU-1-Igγ1 | 150.0 |

TABLE 2

Binding activity against human TLR4/MD2 protein

|  | EC50 value (pM) |
|---|---|
| Fully human ICU-1-Igγ1-LAsh | 521.7 |
| Fully human ICU-1-Igγ1 | 493.5 |

As a result, it was demonstrated that the fully human ICU-1-Igγ1 and the fully human ICU-1-Igγ1-LAsh bind to both the human TLR2 protein and the human TLR4/MD2 protein.

Example 10: Assay of Killed *Pseudomonas aeruginosa*-Induced TNFα Production Inhibition of Bispecific Antibody Binding to Human TLR2 and Human TLR4 on Normal Human Peripheral Blood Mononuclear Cells In order to evaluate the neutralizing activity of the bispecific antibody prepared in Example 8, a killed *Pseudomonas aeruginosa*-induced TNFα production inhibition assay was carried out using human peripheral blood mononuclear cells which endogenously express human TLR2 and human TLR4/MD2. *Pseudomonas aeruginosa* is one of the causative bacteria of sepsis and is known to stimulate TLR2 and TLR4 on human peripheral blood mononuclear cells to produce TNFα (Scand. J. Immunol., 2008, Vol. 67, No. 2, p. 193-203).

30 μL/well of normal human peripheral blood mononuclear cells (Lonza, Inc., CC-2702) was seeded to $1.875 \times 10^4$ cells/well in a 384-well plate (Nunc Inc.), using an RPMI1640 medium (Life Technologies) containing a human serum (Lonza, Inc., 14-490E) suitably prepared at a final concentration of 10 to 30%. Immediately thereafter, 10 μL of the purified antibody fully human ICU-1-Igγ1 diluted in 12 steps in a range from 375 nM to 7.680 fM with an RPMI1640 medium or fully human ICU-1-Igγ1-LAsh diluted in 13 steps in a range from 500 nM to 10.24 fM with an RPMI1640 medium was added and incubated under the conditions of 37° C. and 5% $CO_2$ for 30 minutes. Further, heat-killed *Pseudomonas aeruginosa* PAO-1 of clinical isolates was diluted with an RPMI1640 medium and 10 μL thereof was added to a final concentration of $1 \times 10^6$ CFU (colony forming unit)/mL. As a control, a well to which an RPMI1640 medium had been added instead of an antibody, and a well to which an RPMI1640 medium had been added instead of killed *Pseudomonas aeruginosa* were respectively prepared. After culturing overnight under the conditions of 37° C. and 5% $CO_2$, the culture supernatant was recovered and the concentration of TNFα in the culture supernatant was measured using a commercially available AlphaLISA TNFα kit (PerkinElmer Co., Ltd., AL208C). In addition, the IC50 values of each antibody for killed *Pseudomonas aeruginosa*-induced TNFα production were calculated. In connection with the calculation of an IC50 value, the well to which an RPMI1640 medium had been added instead of an antibody was set as a 0% inhibition control, and the well to which an RPMI1640 medium had been added instead of killed *Pseudomonas aeruginosa* was set as a 100% inhibition control. IC50 values calculated by four-parameter logistic curve fitting are shown below (Table 3).

TABLE 3

Inhibitory activity against killed *Pseudomonas aeruginosa*-induced TNFα production on normal human peripheral blood mononuclear cells

|  | IC50 value (pM) |
|---|---|
| Fully human ICU-1-Igγ1 | 40.00 |
| Fully human ICU-1-Igγ1-LAsh | 17.17 |

As a result, it was demonstrated that the fully human ICU-1-Igγ1 and the fully human ICU-1-Igγ1-LAsh inhibit the TNFα production and have a neutralizing activity against human TLR2 and human TLR4.

Figure 3:
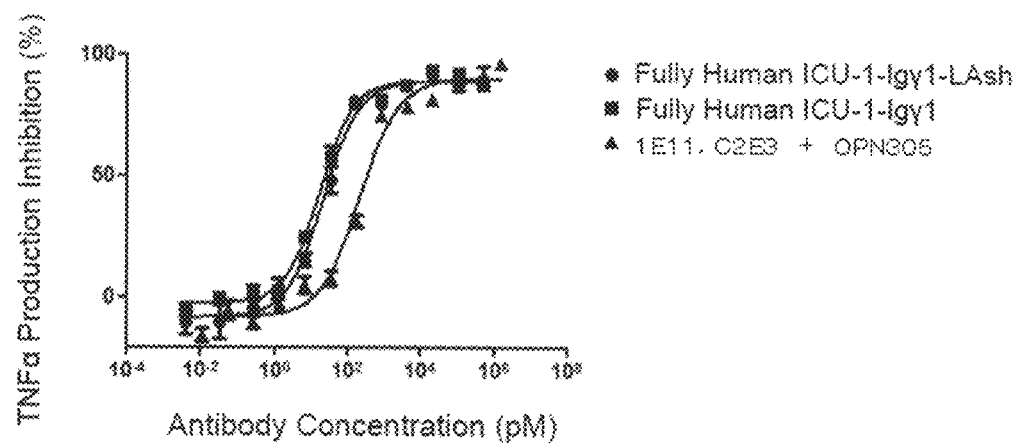
FIG. 3 shows an inhibitory effect of each bispecific antibody on killed *Escherichia coli*-induced TNFα production for normal human peripheral blood mononuclear cells.

Example 11: Inhibition Assay of Killed *Escherichia coli*-Induced TNFα Production on Normal Human Peripheral Blood Mononuclear Cells 30 μL/well of normal human peripheral blood mononuclear cells (Lonza, Inc., CC-2702) was seeded to $1 \times 10^4$ cells/well in a 384-well plate (Nunc Inc.), using an RPMI1640 medium (Life Technologies) containing a human serum (Lonza, Inc., 14-490E) suitably prepared at a final concentration of 10%. Immediately thereafter, 10 μL of the purified fully human ICU-1-Igγ1 or fully human ICU-1-Igγ1-LAsh diluted in 12 steps in a range from 2.500 μM to 20.00 fM with an RPMI1640 medium was added. As a comparative antibody, 10 μL of a mixed solution of a purified anti-human TLR4 antibody 1E11.C2E3 (Patent Document 6) and an anti-human TLR2 antibody OPN305 (Patent Document 3) diluted in 13 steps in a range from 7.758 μM to 52.96 fM with an RPMI1640 medium was added. This was followed by incubation under the conditions of 37° C. and 5% $CO_2$ for 30 minutes. Further, heat-killed *Escherichia coli* (21006) of clinical isolates was diluted with an RPMI1640 medium and 10 μL thereof was added to a final concentration of $1 \times 10^6$ CFU/mL. As a control, a well to which an RPMI1640 medium had been added instead of an antibody, and a well to which an RPMI1640 medium had been added instead of killed *Escherichia coli* were respectively prepared. After culturing overnight under the conditions of 37° C. and 5% $CO_2$, the culture supernatant was recovered and the concentration of TNFα in the culture supernatant was measured using a commercially available AlphaLISA TNFα kit (PerkinElmer Co., Ltd., AL208C). In addition, the IC50 values of each antibody for killed *Escherichia coli*-induced TNFα production were calculated. In connection with the calculation of an IC50 value, the well to which an RPMI1640 medium had been added instead of an antibody was set as a 0% inhibition control, and the well to which an RPMI1640 medium had been added instead of killed *Escherichia coli* was set as a 100% inhibition control. IC50 values calculated by four-parameter logistic curve fitting are shown below (Table 4 and FIG. 3).

TABLE 4

Inhibitory activity against killed *Escherichia coli*-induced TNFα production on normal human peripheral blood mononuclear cells

|  | IC50 value (pM) |
| --- | --- |
| Fully human ICU-1-Igγ1-LAsh | 20.42 |
| Fully human ICU-1-Igγ1 | 16.47 |
| 1E11.C2E3 + OPN305 | 209.2 |

As a result, it was demonstrated that the fully human ICU-1-Igγ1 and the fully human ICU-1-Igγ1-LAsh have a TNFα production inhibitory activity of about 10-fold higher efficacy (potency) than the combined use of 1E11.C2E3 and OPN305.

INDUSTRIAL APPLICABILITY

The bispecific antibody binding to human TLR2 and human TLR4 of the present invention is useful for preventing and treating various diseases which are involved in the human TLR2- and human TLR4-mediated pathogenesis. Further, the polynucleotides, the expression vectors, the transformed host cells, and the methods for producing a bispecific antibody of the present invention are useful for producing the bispecific antibody binding to human TLR2 and human TLR4.

Sequence List Free Text

In the number heading <223> of the sequence list, the description of "Artificial Sequence" is made. Specifically, the base sequence set forth in SEQ ID NO: 1 of the sequence list is the base sequence of the anti-human TLR2 antibody heavy chain-anti-human TLR4 antibody scFv fusion of the fully human ICU-1-Igγ1, and the amino acid sequence set forth in SEQ ID NO: 2 is the amino acid sequence of the anti-human TLR2 antibody heavy chain-anti-human TLR4 antibody scFv fusion encoded by the SEQ ID NO: 1. The base sequence set forth in SEQ ID NO: 3 of the sequence list is the base sequence of the anti-human TLR2 antibody heavy chain-anti-human TLR4 antibody scFv fusion of the fully human ICU-1-Igγ1-LAsh, and the amino acid sequence set forth in SEQ ID NO: 4 is the amino acid sequence of the anti-human TLR2 antibody heavy chain-anti-human TLR4 antibody scFv fusion encoded by the SEQ ID NO: 3. The base sequence set forth in SEQ ID NO: 5 of the sequence list is the base sequence of the anti-human TLR2 antibody light chain of the fully human ICU-1-Igγ1 and fully human ICU-1-Igγ1-LAsh, and the light chain of fully human 31-5F5-2F3.m1 and the amino acid sequence set forth in SEQ ID NO: 6 is the amino acid sequence of the anti-human TLR2 antibody light chain encoded by the SEQ ID NO: 5. The base sequence set forth in SEQ ID NO: 7 of the sequence list is the base sequence of the heavy chain of fully human 31-5F5-2F3.m1, and the amino acid sequence set forth in SEQ ID NO: 8 of the sequence list is the amino acid sequence of the heavy chain encoded by the SEQ ID NO: 7. The amino acid sequence set forth in SEQ ID NO: 9 of the sequence list is the amino acid sequence of a GS linker connecting the C terminal of the heavy chain constant region of the anti-human TLR2 antibody and the N terminal of the anti-human TLR4 antibody scFv included in the fully human ICU-1-Igγ1 and fully human ICU-1-Igγ1-LAsh. The amino acid sequence set forth in SEQ ID NO: 10 of the sequence list is the amino acid sequence of a GS linker connecting the heavy chain variable region and the light chain variable region in the anti-human TLR4 antibody scFv included in the fully human ICU-1-Igγ1 and fully human ICU-1-Igγ1-LAsh.

The invention claimed is:

1. A bispecific antibody that binds to human TLR2 and human TLR4, comprising:
   i) a heavy chain variable region of an anti-human toll-like receptor 2 (TLR2) antibody comprising a CDR1 consisting of amino acid numbers 31 to 35 of SEQ ID NO: 4, a CDR2 consisting of amino acid numbers 50 to 66 of SEQ ID NO: 4 and a CDR3 consisting of amino acid numbers 99 to 109 of SEQ ID NO: 4, and a light chain variable region of an anti-human TLR2 antibody comprising a CDR1 consisting of amino acid numbers 24 to 39 of SEQ ID NO: 6, a CDR2 consisting of amino acid numbers 55 to 61 of SEQ ID NO: 6 and a CDR3 consisting of amino acid numbers 94 to 102 of SEQ ID NO: 6; and
   ii) a heavy chain variable region of an anti-human toll-like receptor 4 (TLR4) antibody comprising a CDR1 consisting of amino acid numbers 521 to 525 of SEQ ID NO: 4, a CDR2 consisting of amino acid numbers 540 to 556 of SEQ ID NO: 4 and a CDR3 consisting of amino acid numbers 589 to 598 of SEQ ID NO: 4, and a light chain variable region of an anti-human TLR4 antibody comprising a CDR1 consisting of amino acid numbers 648 to 658 of SEQ ID NO: 4, a CDR2 consisting of amino acid numbers 674 to 680 of SEQ ID NO: 4 and a CDR3 consisting of amino acid numbers 713 to 721 of SEQ ID NO: 4.

2. The bispecific antibody according to claim 1, comprising
   i) a heavy chain variable region of an anti-human TLR2 antibody consisting of amino acid numbers 1 to 120 of SEQ ID NO: 4, and a light chain variable region of an anti-human TLR2 antibody consisting of amino acid numbers 1 to 113 of SEQ ID NO: 6, and
   ii) a heavy chain variable region of an anti-human TLR4 antibody consisting of amino acid numbers 491 to 609 of SEQ ID NO: 4, and a light chain variable region of an anti-human TLR4 antibody consisting of amino acid numbers 625 to 732 of SEQ ID NO: 4.

3. The bispecific antibody according to claim 2, comprising an anti-human TLR2 antibody and an anti-human TLR4 antibody fragment, wherein
   i) the anti-human TLR2 antibody is an IgG antibody and comprises a heavy chain variable region of an anti-human TLR2 antibody consisting of amino acid numbers 1 to 120 of SEQ ID NO: 4, and a light chain variable region of an anti-human TLR2 antibody consisting of amino acid numbers 1 to 113 of SEQ ID NO: 6, and
   ii) the anti-human TLR4 antibody fragment is a single chain variable region fragment (scFv) and comprises a heavy chain variable region of an anti-human TLR4 antibody consisting of amino acid numbers 491 to 609 of SEQ ID NO: 4, and a light chain variable region of an anti-human TLR4 antibody consisting of amino acid numbers 625 to 732 of SEQ ID NO: 4.

4. A composition comprising the bispecific antibody according to claim 3, a post-translationally modified form of the bispecific antibody, or a combination thereof, and a pharmaceutically acceptable excipient.

5. A composition comprising the bispecific antibody according to claim 2, a post-translationally modified form of the bispecific antibody, or a combination thereof, and a pharmaceutically acceptable excipient.

6. The bispecific antibody according to claim 1, wherein said bispecific antibody is post-translationally modified.

7. The bispecific antibody according to claim 6, wherein said bispecific antibody is post-translationally modified and comprises
   a heavy chain variable region of an anti-human TLR2 antibody consisting of amino acid numbers 1 to 120 of SEQ ID NO: 4 or a post-translationally modified form thereof wherein the glutamic acid of amino acid number 1 of SEQ ID NO: 4 is replaced with pyroglutamic acid, and a light chain variable region of an anti-human TLR2 antibody consisting of amino acid numbers 1 to 113 of SEQ ID NO: 6, and
   a heavy chain variable region of an anti-human TLR4 antibody consisting of amino acid numbers 491 to 609 of SEQ ID NO: 4, and a light chain variable region of an anti-human TLR4 antibody consisting of amino acid numbers 625 to 732 of SEQ ID NO: 4.

8. The bispecific antibody according to claim 7, wherein said bispecific antibody is post-translationally modified and comprises the amino acid sequence of SEQ ID NO: 4 or a post-translationally modified form thereof wherein the glutamic acid of amino acid number 1 of SEQ ID NO: 4 is replaced with pyroglutamic acid, and the amino acid sequence of SEQ ID NO: 6.

9. The bispecific antibody according to claim 8, wherein the heavy chain of the anti-human TLR2 antibody comprises a post-translationally modified form of SEQ ID NO: 4, wherein the glutamic acid of amino acid number 1 of SEQ ID NO: 4 is replaced with pyroglutamic acid.

10. The bispecific antibody according to claim 7, wherein said bispecific antibody is post-translationally modified and comprises an anti-human TLR2 antibody and an anti-human TLR4 antibody fragment, wherein
    i) the anti-human TLR2 antibody is an IgG antibody and comprises the heavy chain variable region of the anti-human TLR2 antibody consisting of amino acid numbers 1 to 120 of SEQ ID NO: 4, or the post-translationally modified form thereof wherein the glutamic acid of amino acid number 1 of SEQ ID NO: 4 is replaced with pyroglutamic acid and the light chain variable region of the anti-human TLR2 antibody consisting of amino acid numbers 1 to 113 of SEQ ID NO: 6, and ii) the anti-human TLR4 antibody fragment is a single chain variable region fragment (scFv) and comprises the heavy chain variable region of an anti-human TLR4 antibody consisting of amino acid numbers 491 to 609 of SEQ ID NO: 4, and the light chain variable region of the anti-human TLR4 antibody consisting of amino acid numbers 625 to 732 of SEQ ID NO: 4.

11. A bispecific antibody comprising an anti-human toll-like receptor 2 (TLR2) antibody heavy chain-anti-human toll-like receptor 4 (TLR4) antibody scFv fusion consisting of the amino acid sequence of SEQ ID NO: 4, and a light chain of anti-human TLR2 antibody consisting of the amino acid sequence of SEQ ID NO: 6.

12. A composition comprising the bispecific antibody according to claim 11, a post-translationally modified form of the bispecific antibody, or a combination thereof, and a pharmaceutically acceptable excipient.

13. A polynucleotide comprising a nucleotide sequence encoding the amino acid sequence of SEQ ID NO: 4.

14. An expression vector comprising the polynucleotide according to claim 13.

15. A polynucleotide comprising a nucleotide sequence encoding the amino acid sequence of SEQ ID NO: 6.

16. An expression vector comprising the polynucleotide according to claim 15.

17. A host cell selected from the group consisting of the following (a) to (d):

(a) a host cell transformed with a first expression vector comprising a polynucleotide sequence encoding the amino acid sequence of SEQ ID NO: 4; and a second expression vector comprising a polynucleotide sequence encoding the amino acid sequence of SEQ ID NO: 6;

(b) a host cell transformed with an expression vector comprising a polynucleotide sequence encoding the amino acid sequence of SEQ ID NO: 4, and a polynucleotide sequence encoding the amino acid sequence of SEQ ID NO: 6;

(c) a host cell transformed with an expression vector comprising a polynucleotide sequence encoding the amino acid sequence of SEQ ID NO: 4; and (d) a host cell transformed with an expression vector comprising a polynucleotide sequence encoding the amino acid sequence of SEQ ID NO: 6.

18. A method for producing a bispecific antibody that binds to human TLR2 and human toll-like receptor 4 (TLR4), comprising culturing host cell(s) according to claim 17 to express a bispecific antibody that binds to human TLR2 and human TLR4.

19. A bispecific antibody that binds to human TLR2 and human TLR4, produced by the method according to claim 18.

* * * * *